US012751795B2

(12) United States Patent
Ahn

(10) Patent No.: US 12,751,795 B2
(45) Date of Patent: Oct. 6, 2026

(54) METHOD FOR DERIVING CEPHALOMETRIC PARAMETERS FOR ORTHODONTIC DIAGNOSIS BASED ON MACHINE LEARNING FROM THREE-DIMENSIONAL (3D) CBCT IMAGE TAKEN IN NATURAL HEAD POSITION

(71) Applicant: AINSIGHT INC., Hwaseong-si (KR)

(72) Inventor: Jang Hoon Ahn, Seoul (KR)

(73) Assignee: AINSIGHT INC., Hwaseong-si (KR)

( * ) Notice: Subject to any disclaimer, the term of this patent is extended or adjusted under 35 U.S.C. 154(b) by 190 days.

(21) Appl. No.: 18/292,309

(22) PCT Filed: Aug. 19, 2021

(86) PCT No.: PCT/KR2021/011012
§ 371 (c)(1),
(2) Date: Jan. 25, 2024

(87) PCT Pub. No.: WO2023/013805
PCT Pub. Date: Feb. 9, 2023

(65) Prior Publication Data

US 2025/0090272 A1 Mar. 20, 2025

(30) Foreign Application Priority Data

Aug. 4, 2021 (KR) ........................ 10-2021-0102733

(51) Int. Cl.
*G06T 7/73* (2017.01)
*A61C 7/00* (2006.01)
(Continued)

(52) U.S. Cl.
CPC .............. *A61C 7/002* (2013.01); *A61C 19/05* (2013.01); *G06T 7/0012* (2013.01); *G06T 7/73* (2017.01);
(Continued)

(58) Field of Classification Search
CPC ......... A61C 7/002; A61C 19/05; A61C 11/00; A61C 19/04; A61C 19/045; A61C 7/00;
(Continued)

(56) References Cited

U.S. PATENT DOCUMENTS 10,898,298 B1 1/2021 Raslambekov
11,995,820 B2 * 5/2024 Kim ........................ A61B 6/501
(Continued)

FOREIGN PATENT DOCUMENTS

CN 110326023 A 10/2019
CN 110782974 A 2/2020
(Continued)

OTHER PUBLICATIONS

Juneja M. et al, "A review on cephalometric landmark detection techniques", Biomedical Signal Processing and Control, University Institute of Engineering and Technology, Panjab University, Chandigarh, India, pp. 1-14, Feb. 20, 2021. (Year: 2021).*
(Continued)

*Primary Examiner* — Jose L Couso
(74) *Attorney, Agent, or Firm* — Park, Kim & Suh, LLC

(57) ABSTRACT

The present invention relates to a method for deriving cephalometric parameters for orthodontic diagnosis based on machine learning. More specifically, the present invention relates to a method for deriving cephalometric parameters for orthodontic diagnosis based on machine learning, wherein a machine-learning algorithm is applied after acquiring a 3D cone-beam computer tomography (CBCT) image of a subject data taken in a natural head position, and a plurality of cephalometric landmarks can be precisely and rapidly digitized on the 3D CBCT image in order to derive 13 diagnosis parameters for precise orthodontic diagnosis.

20 Claims, 12 Drawing Sheets

(51) Int. Cl.

| | |
|---|---|
| ***A61C 19/05*** | (2006.01) |
| ***G06T 7/00*** | (2017.01) |
| ***G16H 30/40*** | (2018.01) |
| ***G16H 50/20*** | (2018.01) |
| *A61B 6/51* | (2024.01) |

(52) U.S. Cl.

CPC ............. *G16H 30/40* (2018.01); *G16H 50/20* (2018.01); *A61B 6/51* (2024.01); *G06T 2200/04* (2013.01); *G06T 2207/10081* (2013.01); *G06T 2207/20081* (2013.01); *G06T 2207/20084* (2013.01); *G06T 2207/30036* (2013.01); *G06T 2207/30242* (2013.01)

(58) Field of Classification Search

CPC ..... G06T 7/0012; G06T 7/73; G06T 2200/04; G06T 2207/10081; G06T 2207/20081; G06T 2207/20084; G06T 2207/30036; G06T 2207/30242; G06T 3/4046; G06T 5/60; G06T 9/002; G06T 2207/20076; G06T 2211/441; G06T 2207/10072; G06T 2207/10116; G06T 2207/30008; G06T 7/74; G06T 7/75; G06T 7/60; G06T 7/62; G16H 30/40; G16H 50/20; G16H 50/30; G16H 50/50; G16H 20/40; G16H 30/20; A61B 6/51; A61B 5/1072; A61B 5/1075; A61B 5/1121; A61B 5/1128; A61B 5/7264; A61B 6/032; A61B 6/00; A61B 6/03; A61B 6/5217; A61B 5/00009; A61B 1/24; A61B 2034/101; A61B 2034/105; A61B 34/10; A61B 5/055; A61B 6/463; A61B 6/5235; A61B 6/025; A61B 6/501; A61B 6/466; G06N 3/045; G06N 20/00; G06N 3/02; G06N 3/08–088; G06N 3/04; G06N 3/0445; G06N 3/0454; G06N 3/0464; G06N 3/4046; G06N 3/4053; G06N 3/049; G06N 3/0499; G06N 7/00; G06N 7/01; G06K 7/1482; G06V 10/454; G06V 10/54; G06V 10/7764; G06V 10/774; G06V 10/82; G06V 10/84; G06V 20/41; G06V 30/18057; G06V 20/698; G06V 30/19173; G06V 30/194; G06V 2201/003; G06V 10/751; G06V 2201/03; G06V 40/162; G06V 40/165; G06V 20/64; G06V 40/169; G06F 18/213; G06F 18/214; G06F 18/22; G06F 18/241; G06F 18/24; G06F 18/2411; G06F 18/2415; G06F 18/253; G06F 30/27; Y10S 128/925

See application file for complete search history.

(56) References Cited

U.S. PATENT DOCUMENTS

| | | | | |
|---|---|---|---|---|
| 2013/0022252 | A1* | 1/2013 | Chen | G06T 3/4038 382/131 |
| 2013/0022254 | A1* | 1/2013 | Chen | G06T 7/149 382/128 |
| 2015/0265374 | A1* | 9/2015 | Masoud | G06V 40/171 382/128 |
| 2016/0278721 | A1 | 9/2016 | Im et al. | |
| 2018/0061054 | A1* | 3/2018 | Abraham | G06T 7/337 |
| 2018/0184989 | A1 | 7/2018 | Inglese et al. | |
| 2019/0328489 | A1* | 10/2019 | Capron-Richard | A61B 6/463 |
| 2020/0035351 | A1 | 1/2020 | Kim | |
| 2020/0286223 | A1 | 9/2020 | Kim et al. | |
| 2021/0153976 | A1* | 5/2021 | Chen | A61C 9/004 |
| 2021/0244372 | A1* | 8/2021 | Inglese | A61B 6/463 |

FOREIGN PATENT DOCUMENTS

| | | | | |
|---|---|---|---|---|
| CN | 111083922 | A | 4/2020 | |
| JP | 2014-151196 | A | 8/2014 | |
| JP | 2020-513918 | A | 5/2020 | |
| JP | 2020-534037 | A | 11/2020 | |
| KR | 10-2014-0114308 | A | 9/2014 | |
| KR | 10-2015-0072078 | A | 6/2015 | |
| KR | 10-2019-0067609 | A | 6/2019 | |
| KR | 10-2019-0107683 | A | 9/2019 | |
| KR | 10-2020-0023703 | A | 3/2020 | |
| KR | 10-2021-0017414 | A | 2/2021 | |
| KR | 20210066074 | A * | 6/2021 | G16H 30/40 |
| WO | 2017/069231 | A1 | 4/2017 | |
| WO | 2020/067005 | A1 | 4/2020 | |

OTHER PUBLICATIONS

"Cephalometric analysis" (https://www.oxfordreference.com/display/10.1093/oi/authority.20110803095559375), Feb. 22, 1999, downloaded from the internet on Dec. 3, 2025. (Year: 1999).*

"Cephalometric analysis", Wikipedia, which list the Oxford Reference as the first reference (and which is provided herewith), downloaded from the internet on Dec. 3, 2025. (Year: 2025).*

International Search Report in International Application No. PCT/KR2021/011012, dated Apr. 29, 2022, 3 pages.

Rouh Hwai Wang, et al., "Three-dimensional cephalometry for orthognathic planning: Normative data and analyses", Journal of the Formosan Medical Association, Excerpta Medica Asia, Hong Kong, vol. 119, No. 1, Apr. 16, 2019, pp. 191-203, XP086037015, ISSN: 0929-6646, retrieved on https://doi.org/10.1016/j.jfma.2019.04.001, 13 pages.

Youngju Park, et al., "Assessment of anterior-posterior jaw relationships in Korean adults using the nasion true vertical plane in cone-beam computed tomorgrapgy images", The Korean Journal of Orthodontics, 2016; 46(3), May 20, 2016, pISSN 2234-7518, eISSN 2005-37 2x, PP. 163-170, https://doi.org/10.4041/kjod.2016.46.3.163, 8 pages.

Zhong Xiao-Long, et al., "Evaluation of true horizontal plane under natural head position as a basis for cephalometric analysis", China Academic Journal Electronic Pulishing House, Journal of Clinical Stomatology, 2024; 20(12), Dec. 30, 2004, pp. 749-751, 3 pages.

* cited by examiner

FIG. 12

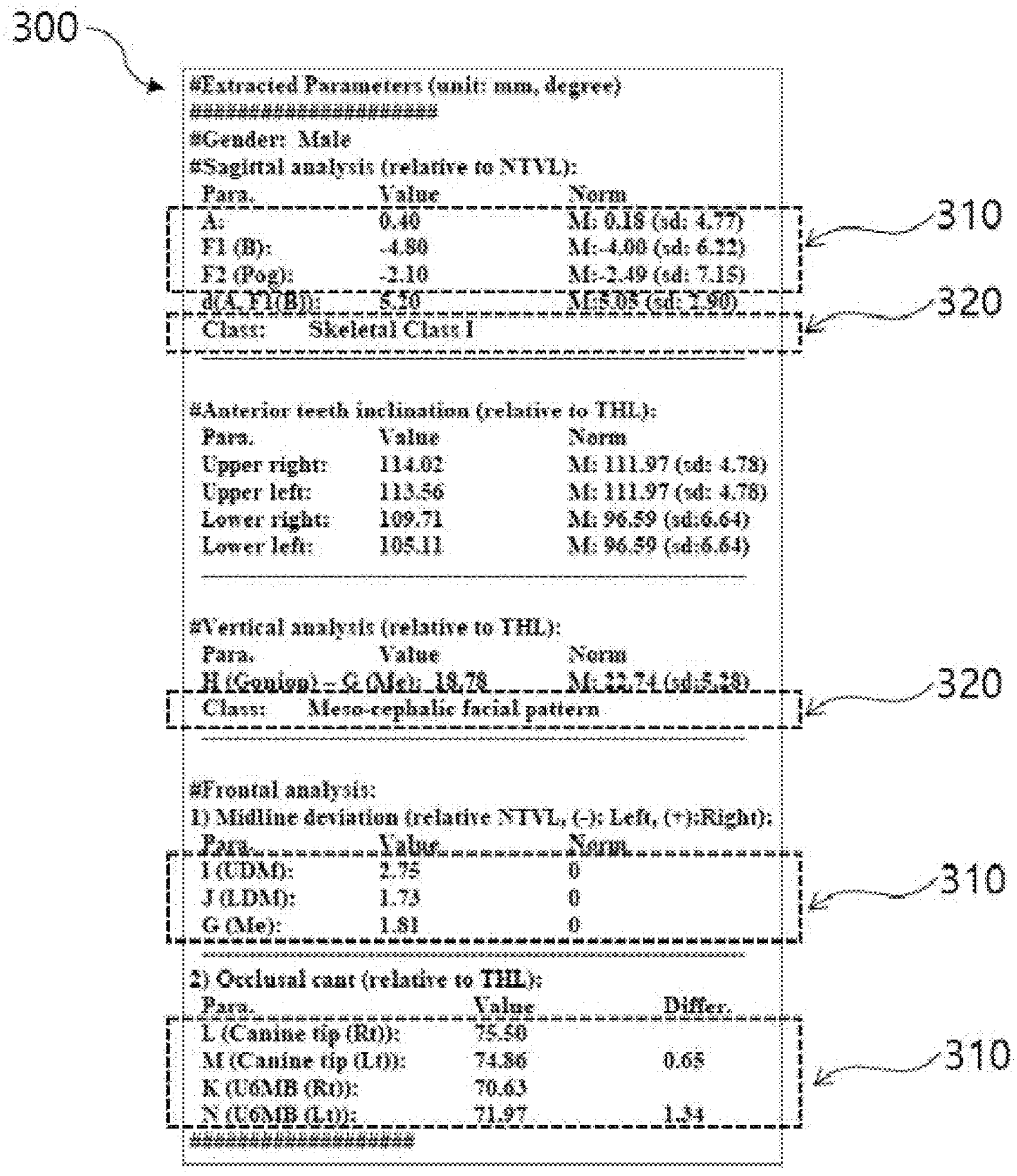

#Extracted Parameters (unit: mm, degree)
##############
#Gender: Male
#Sagittal analysis (relative to NTVL):

| Para. | Value | Norm |
|---|---|---|
| A: | 0.40 | M: 0.18 (sd: 4.77) |
| F1 (B): | -4.80 | M:-4.00 (sd: 6.22) |
| F2 (Pog): | -2.10 | M:-2.49 (sd: 7.15) |
| d(A,Y)(B)): | 5.20 | M:5.08 (sd: 7.90) |

Class: Skeletal Class I

#Anterior teeth inclination (relative to THL):

| Para. | Value | Norm |
|---|---|---|
| Upper right: | 114.02 | M: 111.97 (sd: 4.78) |
| Upper left: | 113.56 | M: 111.97 (sd: 4.78) |
| Lower right: | 109.71 | M: 96.59 (sd:6.64) |
| Lower left: | 105.11 | M: 96.59 (sd:6.64) |

#Vertical analysis (relative to THL):

| Para. | Value | Norm |
|---|---|---|
| H (Gonion) - G (Me): | 18.78 | M: 22.74 (sd:5.28) |

Class: Meso-cephalic facial pattern

#Frontal analysis:
1) Midline deviation (relative NTVL, (-): Left, (+):Right):

| Para. | Value | Norm |
|---|---|---|
| I (UDM): | 2.75 | 0 |
| J (LDM): | 1.73 | 0 |
| G (Me): | 1.81 | 0 |

2) Occlusal cant (relative to THL):

| Para. | Value | Differ. |
|---|---|---|
| L (Canine tip (Rt)): | 75.50 | |
| M (Canine tip (Lt)): | 74.86 | 0.65 |
| K (U6MB (Rt)): | 70.63 | |
| N (U6MB (Lt)): | 71.97 | 1.34 |

##############

METHOD FOR DERIVING CEPHALOMETRIC PARAMETERS FOR ORTHODONTIC DIAGNOSIS BASED ON MACHINE LEARNING FROM THREE-DIMENSIONAL (3D) CBCT IMAGE TAKEN IN NATURAL HEAD POSITION

CROSS-REFERENCE TO RELATED APPLICATIONS

This application is a National Phase Application of PCT International Application No. PCT/KR2021/011012, which was filed on Aug. 19, 2021, and which claims priority from Korean Patent Application No. 10-2021-0102733 filed on Aug. 4, 2021. The disclosures of the above patent application are incorporated herein by reference in their entirety.

TECHNICAL FIELD

The present invention relates to a method deriving cephalometric parameters for orthodontic diagnosis based on machine learning. More specifically, the present invention relates to a method deriving cephalometric parameters for orthodontic diagnosis based on machine learning, which is capable of obtaining a 3D CBCT image of a patient from cone beam computed tomography (CBCT) image data in a state of natural head position and precisely and quickly detecting a plurality of cephalometric landmarks on the 3D CBCT image in order to derive 13 parameters for orthodontic diagnosis by machine learning algorithms and image analysis processing technology being applied.

BACKGROUND ART

In general, the condition in which the teeth are not aligned correctly and the upper and lower teeth are misaligned is referred to as malocclusion, and orthodontic treatment may be performed to correct such malocclusion into normal occlusion. Meanwhile, it is required to detect anatomical cephalometric landmarks that are predetermined anatomically in a 3D CBCT image of a patient for precise diagnosis or treatment planning for orthodontic treatment.

Recently, a three-dimensional (3D) cone beam computed tomography (CBCT) image has been obtained from the dental image data of a patient's head captured by a CBCT device without problems such as a screen distortion phenomenon or unclearness in the existing X-ray image, and a study is being conducted to detect cephalometric landmarks for deriving parameters for orthodontic diagnosis based on the CBCT image. In particular, as a method of analyzing a cone beam computed tomography (CBCT) image, recent studies have proposed a method of identifying the anteroposterior skeletal relationship and the degree of protrusion of teeth using the nasion true vertical plane (NTVP) that passes through nasion that is the most concave point between a frontal bone and a nasal bone, and is perpendicular to the ground, and the true horizontal plane (THP) that passes through nasion (N) and is horizontal to the ground, and the like.

In the related art, a skilled operator, such as a dental practitioner, has to manually detect a large number of cephalometric landmarks of approximately 50 or more on a plurality of CBCT images in order to derive parameters for orthodontic diagnosis. In this method, the method of detecting the cephalometric landmarks and the accuracy of detection varies depending on the operator's proficiency, making it difficult to make an accurate correction diagnosis, and it takes a long period of time of approximately 30 minutes or more to detect the cephalometric landmarks, reducing the efficiency of orthodontic treatment.

To solve this problem, machine learning algorithm is introduced in the field of dentistry: orthodontic diagnosis, and the 3D CBCT image of a patient is obtained from 3D cone beam computed tomography (CBCT) image data in a state of natural head position. For precise orthodontic diagnosis, a plurality of cephalometric landmarks on the 3D CBCT image are detected precisely and quickly, and a reduced number of parameters are derived than the related art. Accordingly, there is a strong need for a method deriving cephalometric parameters for orthodontic diagnosis based on machine learning that can improve the efficiency of orthodontic treatment.

DISCLOSURE

Technical Problem

The present invention is directed to provide a method deriving cephalometric parameters for orthodontic diagnosis based on machine learning that is capable of improving the efficiency of orthodontic treatment by obtaining a 3D CBCT image of a patient from a cone beam computed tomography (CBCT) image data in a state of natural head position with machine learning algorithm being applied and precisely and quickly deriving a plurality of cephalometric landmarks on the 3D CBCT image to derive 13 parameters, which are reduced from the related art, for precise orthodontic diagnosis.

Technical Solution

To achieve the aforementioned objects, the present invention provides a method deriving cephalometric parameters for orthodontic diagnosis based on machine learning, using a 3D CBCT image for orthodontic diagnosis extracted from a step of obtaining a 3D CBCT image for diagnosis which includes a CBCT image in a sagittal plane, a CBCT image in a coronal plane, a dental panoramic image, and an incisor image in a cross-sectional view, respectively, for a patient from a three-dimensional (3D) cone beam computed tomography (CBCT) image data captured of the patient's head at a natural head position, the method may comprise: detecting, based on machine learning algorithm, a plurality of cephalometric landmarks on the 3D CBCT image to derive 13 parameters for orthodontic diagnosis; and deriving 13 parameters corresponding to distances or angles between the detected plurality of cephalometric landmarks.

Here, in order to provide information on the orthodontic diagnosis, the 13 parameters may include a degree of protrusion of a maxilla, a degree of protrusion of a mandible, a degree of protrusion of chin, a degree of displacement of a center of a mandible, a degree of displacement of the midline of upper central incisors, and a degree of displacement of the midline of lower central incisors, a vertical distance from the true horizontal plane (THP) passing through nasion, which is the most concave point between a frontal bone and a nasal bone, to a tip of a right upper canine, a vertical distance from the THP to a tip of a left upper canine, a vertical distance from the THP to a right upper first molars, a vertical distance from the THP to a left upper first molars, a degree of inclination of a upper central incisor, a degree of inclination of a lower central incisor, and a degree of inclination of the mandible with respect to the THP.

In addition, the machine learning algorithm may detect the plurality of cephalometric landmarks to derive the 13 parameters by dividing the CBCT image in the sagittal plane into a region provided between a frontal bone portion and nasion, a region between nasion and upper teeth, a region between lower teeth and the lowest point of the mandible (menton, Me), and a region between menton of the mandible and an articular bone of jaw.

Further, the machine learning algorithm may detect the plurality of cephalometric landmarks to derive the 13 parameters by dividing the CBCT image in the coronal plane into a region between a frontal bone portion and nasion and a mandible region.

In addition, machine learning algorithm may include: applying a region based convolutional neural network (R-CNN) machine learning model to the dental panoramic image to detect individual regions of entire set of teeth; detecting, for each detected individual region of the entire set of teeth, teeth landmarks representing positions of the teeth; analyzing the positions of the detected teeth landmarks to classify the entire set of teeth into upper teeth and lower teeth; numbering each of right upper teeth, left upper teeth, right lower teeth, and left lower teeth sequentially based on a horizontal distance from the midline of a facial portion to the detected teeth landmarks; and analyzing the numbered teeth to detect a plurality of cephalometric landmarks for deriving a parameter from a specific tooth, including an incisor, a canine, and a first molar.

Further, the machine learning algorithm may detect nasion, which is the most concave point between a frontal bone and a nasal bone, and A-point (A), which is the deepest portion of a line connecting an anterior nasal spine in the maxilla and a prosthion, in the CBCT image in the sagittal plane, and wherein the degree of protrusion of a maxilla is derived by measuring a distance between the nasion true vertical plane (NTVP), which is a vertical plane passing through nasion, and A-point.

In addition, the machine learning algorithm may detect nasion, which is the most concave point between a frontal bone and a nasal bone, and B-point, which is the deepest portion connecting an infradentale and Pog, which is the most prominent point of chin, in the CBCT image in the sagittal plane, and wherein the degree of protrusion of the mandible is derived by measuring a distance between the nasion true vertical plane (NTVP), which is a vertical plane passing through nasion, and B-point.

In addition, the machine learning algorithm may detect nasion, which is the most concave point between a frontal bone and a nasal bone, and pogonion, which is the most prominent point of chin, in the CBCT image in the sagittal plane, and wherein the degree of protrusion of chin is derived by measuring a distance between the nasion true vertical plane (NTVP), which is a vertical plane passing through nasion, and pogonion.

In addition, the machine learning algorithm may detect nasion, which is the most concave point between a frontal bone and a nasal bone, and menton, which is the lowest point of the mandible, in the CBCT image in the coronal plane, and wherein the degree of displacement of a center of the mandible is derived by measuring a distance between the nasion true vertical plane (NTVP), which is a vertical plane passing through nasion, and menton.

In addition, the machine learning algorithm may detect nasion, which is the most concave point between a frontal bone and a nasal bone in the CBCT image in the coronal plane, and a midpoint of upper central incisors in the dental panoramic image, and wherein the degree of displacement of the midline of the upper central incisors is derived by measuring a distance between the nasion true vertical plane (NTVP), which is a vertical plane passing through nasion, and the midpoint of the upper central incisors.

In addition, the machine learning algorithm may detect nasion, which is the most concave point between a frontal bone and a nasal bone in the CBCT image in the coronal plane, and a central point of lower central incisors in the dental panoramic image, and wherein the degree of displacement of the midline of the lower central incisors is derived by measuring a distance between the nasion true vertical plane (NTVP), which is a vertical plane passing through nasion, and the midpoint of the lower central incisors.

In addition, the machine learning algorithm may detect nasion, which is the most concave point between a frontal bone and a nasal bone in the CBCT image in the coronal plane, and the cusp tip of the right upper canine in the dental panoramic image, and wherein the vertical distance between the true horizontal plane (THP), which is a horizontal plane passing through nasion, and the cusp tip of the right upper canine is derived.

In addition, the machine learning algorithm may detect nasion, which is the most concave point between a frontal bone and a nasal bone in the CBCT image in the coronal plane, and the cusp tip of the left upper canine in the dental panoramic image, and wherein the vertical distance between the true horizontal plane (THP), which is a horizontal plane passing through nasion, and the cusp tip of the left upper canine is derived.

In addition, the machine learning algorithm may detect nasion, which is the most concave point between a frontal bone and a nasal bone in the CBCT image in the coronal plane, and the mesio-buccal cusp tip of a right upper first molar in the dental panoramic image, and wherein, through a distance between the true horizontal plane (THP), which is a horizontal plane passing through nasion, and the mesio-buccal cusp tip of the right upper first molar, the vertical distance from the THP to the right upper first molars is derived.

In addition, the machine learning algorithm may detect nasion, which is the most concave point between a frontal bone and a nasal bone in the CBCT image in the coronal plane, and the mesio-buccal cusp tip of a left upper first molar in the dental panoramic image, and wherein, through a distance between the true horizontal plane (THP), which is a horizontal line passing through nasion, and the mesio-buccal cusp tip of the left upper first molar, the vertical distance from the THP to the left upper first molar is derived.

In addition, the machine learning algorithm may detect nasion, which is the most concave point between a frontal bone and a nasal bone in the CBCT image in the coronal plane, and the crown tip of the upper incisor and the root tip of the upper incisor in the incisor image in a cross-sectional view, and wherein the degree of inclination of the upper central incisor is derived through an angle between the true horizontal plane (THP), which is a horizontal plane passing through nasion, and a vector connecting the crown tip of the upper incisor and the root tip of the upper incisor.

In addition, the machine learning algorithm may detect menton, which is the lowest point in the mandible, and gonion, which is a point of maximum curvature in the mandibular angle, in the CBCT image in the sagittal plane, and the crown tip of the lower incisor and the root tip of the lower incisor in the incisor image in a cross-sectional view, and wherein the degree of inclination of the lower central incisor is derived through an angle between a MeGo line connecting menton and gonion and a vector connecting the crown tip of the lower incisor and the root tip of the lower incisor.

In addition, the machine learning algorithm may detect nasion, which is the most concave point between a frontal bone and a nasal bone, menton, which is the lowest point in the mandible, and gonion, which is a point of maximum curvature in the mandibular angle, in the CBCT image in the sagittal plane, and wherein, through an angle between the true horizontal plane (THP), which is a horizontal plane passing through nasion, and a MeGo line connecting menton and gonion, the degree of inclination of the mandible with respect to the THP is derived.

The present invention may further include diagnosing a facial profile of the patient or an occlusal state in response to the derived 13 parameters.

Here, when the patient's occlusal state may be diagnosed corresponding to the derived 13 parameters, a state in which an antero-posterior occlusal position of the maxilla and mandible is in a relatively normal category, a state in which the maxilla relatively protrudes relative to the mandible, and a state in which the mandible relatively protrudes relative to the maxilla are classified and diagnosed, respectively.

In addition, when a facial profile of the patient may be diagnosed corresponding to the derived 13 parameters, a state in which a length of the facial portion is in a normal category, a state in which the length of the facial portion is shorter than the normal category, and a state in which the length of the facial portion is longer than the normal category are classified and diagnosed respectively.

Furthermore, the present invention provide a program for deriving cephalometric parameters for orthodontic diagnosis that is installed on a computing device or a computable cloud server and is programmed to automatically perform of: detecting a plurality of cephalometric landmarks as output data after obtaining the 3D CBCT image for orthodontic diagnosis results in the method deriving cephalometric parameters for orthodontic diagnosis; and deriving 13 parameters corresponding to distances or angles between the detected plurality of cephalometric landmarks.

Advantageous Effects

According to the method of deriving cephalometric parameters for orthodontic diagnosis based on machine learning, in accordance with the present invention, a plurality of 3D CBCT images for diagnosis, including CBCT images in the direction of the sagittal plane and the coronal plane, an incisor image in a cross-sectional view, and a dental panoramic image of a patient, are extracted from image data captured by cone beam computed tomography (CBCT) at a natural head position with the machine learning algorithm being applied. The positions of predetermined cephalometric landmarks for extracting the parameters from the image are automatically detected, thereby enabling the orthodontic diagnosis operation to be processed very quickly, at a level within approximately tens of seconds.

According to the method of deriving cephalometric parameters for orthodontic diagnosis based on machine learning in accordance with the present invention, based on the cephalometric landmarks detected on a cone beam computed tomography (CBCT) image taken in a natural head position, 13 parameters for diagnosis are selected and derived, which are reduced from the related art, in order to smoothly identify the anterior-posterior skeletal relationship and the degree of protrusion of teeth in the sagittal plane. Accordingly, the machine learning algorithm for detecting the cephalometric landmarks can be simplified and the time required for orthodontic diagnosis can be shortened.

Furthermore, according to the method deriving cephalometric parameters for orthodontic diagnosis based on machine learning in accordance with the present invention, a 3D CBCT image for diagnosis is extracted through the machine learning algorithm, and cephalometric landmarks on the image are detected. As a result, 13 parameters are derived, and not only the facial profile of the patient or occlusal state is automatically diagnosed, but also the range of applications can be further expanded, such as automatically designing a customized dental correction device for the patient in response to the derived parameters.

DESCRIPTION OF DRAWINGS

FIGS. 11 and 12 illustrate a graphic user interface (GUI) screen with the method deriving cephalometric parameters for orthodontic diagnosis based on machine learning according to the present invention being applied.

BEST MODES OF THE INVENTION

Figure 1:
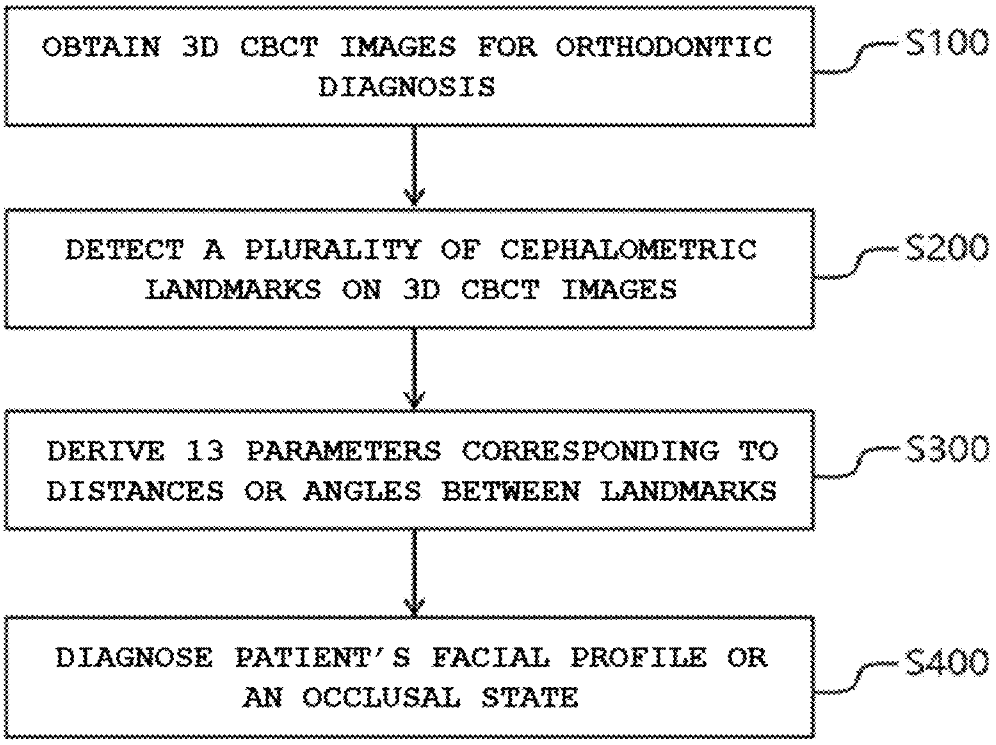
FIG. 1 illustrates a flowchart of a method deriving cephalometric parameters for orthodontic diagnosis based on machine learning according to the present invention.

Hereinafter, exemplary embodiments of the present invention will be described in detail with reference to the accompanying drawings. However, the present invention is not limited to the exemplary embodiments described below and may be specified as other aspects. On the contrary, the embodiments introduced herein are provided to make the disclosed content thorough and complete, and sufficiently transfer the spirit of the present invention to those skilled in the art. Like reference numerals indicate like constituent elements throughout the specification.

FIG. 1 illustrates a flowchart of a method deriving cephalometric parameters for orthodontic diagnosis based on machine learning according to the present invention.

As illustrated in FIG. 1, a method deriving cephalometric parameters based on machine learning according to the present invention includes a step (S100) of obtaining 3D CBCT images for diagnosis that includes CBCT images in the directions of a sagittal plane and a coronal plane, respectively, a CBCT image in a vertical direction, a dental panoramic image, and an incisor image in a cross-sectional view from cone beam computed tomography (CBCT) image data taken by a dental CBCT device while the patient's head is positioned at a natural head position, a step (S200) of detecting a plurality of cephalometric landmarks on the 3D CBCT image for diagnosis to derive 13 parameters for orthodontic diagnosis based on machine learning algorithm, and a step (S300) of deriving 13 parameters corresponding to distances or angles between the detected plurality of cephalometric landmarks.

In addition, the method deriving cephalometric parameters based on machine learning according to the present invention may further include a step (S400) of diagnosing the patient's facial profile or an occlusal state of the patient in response to the derived 13 parameters.

Figure 2:
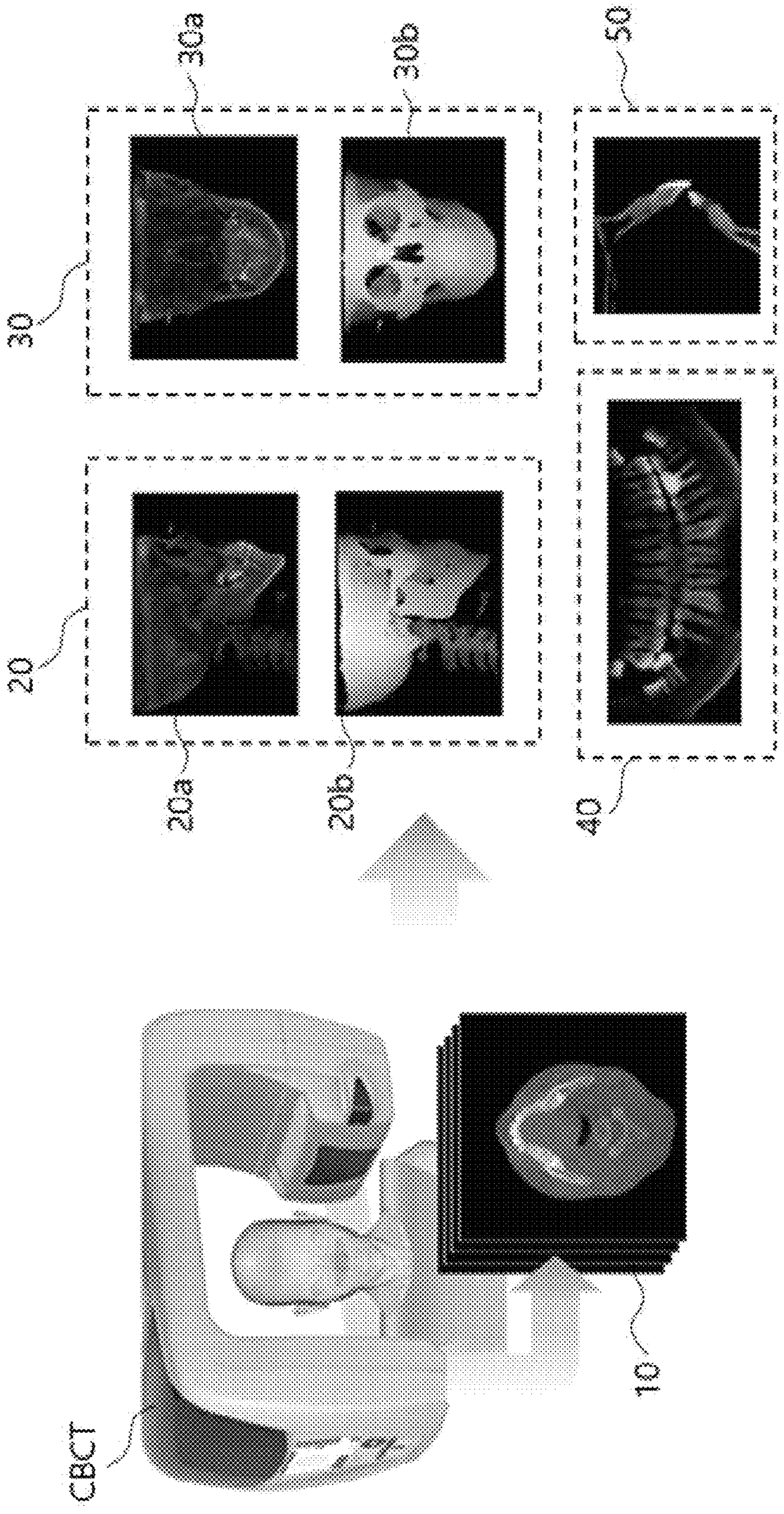
FIG. 2 illustrates a process obtaining a 3D CBCT image for diagnosis of a patient in the method deriving cephalometric parameters for orthodontic diagnosis based on machine learning according to the present invention.

FIG. 2 illustrates a process obtaining a 3D CBCT image for diagnosing a patient by the method deriving cephalometric parameters based on machine learning according to the present invention.

As illustrated in FIG. 2, in step S100 obtaining the 3D CBCT images for diagnosis, a plurality of 3D CBCT images for diagnosis including a CBCT image 20 in the direction of the sagittal plane that is divided into left and right with respect to the patient, a CBCT image 30 in the direction of the coronal plane that is divided into front and rear with respect to the patient, a dental panoramic image 40, and an incisor image in a cross-sectional view 50 are each obtained from CBCT image data 10 captured and obtained by the cone beam computed tomography device.

In step S100 obtaining the 3D CBCT image for diagnosis, a dental cone beam computed tomography (CBCT) device may be used to obtain three-dimensional (3D) CBCT image data in the entire region for the patient. The CBCT image data 10 may satisfy a digital imaging and communications in medicine (DICOM) standard by the machine learning algorithm, and the CBCT image data may obtain the 3D CBCT image for diagnosis by an image extraction function input to the machine learning algorithm or an image extraction function of a general DICOM viewer.

Here, the CBCT image data 10 may be extracted as a 3D CBCT image for diagnosis, including the CBCT image 20 in the sagittal plane, the CBCT image 30 in the coronal plane, the dental panoramic image 40, and the incisor image in a cross-sectional view 50. Among them, the CBCT image 20 in the sagittal plane and the CBCT image 30 in the coronal plane may be extracted by being categorized into a bone mode image 20*a* in the sagittal plane and a bone mode image 30*a* in the coronal plane, which are modes in which the inside of the skull bone tissue is projected and represented, respectively, and may be extracted by being categorized into a depth mode image 20*b* in the sagittal plane and a depth mode image 30*b* in the coronal plane, which are modes in which the outside of the skull bone tissue is represented in consideration of the depth, density, or the like of the skull bone tissue of the patient.

Then, in step S200 of detecting a plurality of cephalometric landmarks for orthodontic diagnosis may be automatically detected on the 3D CBCT image for diagnosis through the machine learning algorithm. In the related art, a skilled operator such as a dentist manually designated cephalometric landmarks on the 3D CBCT image for diagnosis, but such a method causes deviations in accuracy depending on the operator's proficiency, and it takes a long time of approximately 30 minutes to one hour to detect the cephalometric landmarks, which leads to a decrease in orthodontic treatment efficiency.

Meanwhile, in the present invention, machine learning algorithm including a facial profile automatic analysis model and a region based convolutional neural network (R-CNN) may be used to automatically detect a plurality of predetermined cephalometric landmarks on the 3D CBCT image for diagnosis. As a result, in step S300 deriving the 13 parameters, 13 parameters selected to correspond to distances or angles defined between a plurality of cephalometric landmarks are derived, and through the derived 13 parameters, the facial state or oral state of the patient is detected to perform the orthodontic diagnosis for the patient.

In the related art, it is necessary to detect a large number of head cephalometric landmarks of approximately 50 or more in the 3D CBCT image for diagnosis in order to derive the parameters for orthodontic diagnosis, but in the present invention, 13 parameters are strictly selected to efficiently diagnose the patient's sagittal anterior-posterior skeletal relationship, occlusal state, and the degree of protrusion of teeth, thereby dramatically reducing the number of cephalometric landmarks that need to be detected to derive the parameters. Accordingly, the machine learning algorithm for implementing this is simplified, and the time required for orthodontic diagnosis can be shortened.

In a method of analyzing cephalometric measurements for the purpose of orthodontic diagnosis, instead of using the Wits appraisal, Rickett appraisal, McNamara appraisal, or the like, which have been widely practiced, the present inventors have devised the method that can easily diagnose the patient's anterior-posterior jaw relationship while dramatically reducing the number of cephalometric landmarks using the nasion true vertical plane (NTVP) or the true horizontal plane (THP) that passes through nasion (N), which is generally a portion from which a nose bridge begins, in an image taken at a natural head position, and the process detecting a plurality of cephalometric landmarks can be performed quickly and efficiently by applying the method to machine learning algorithm.

Figure 3:
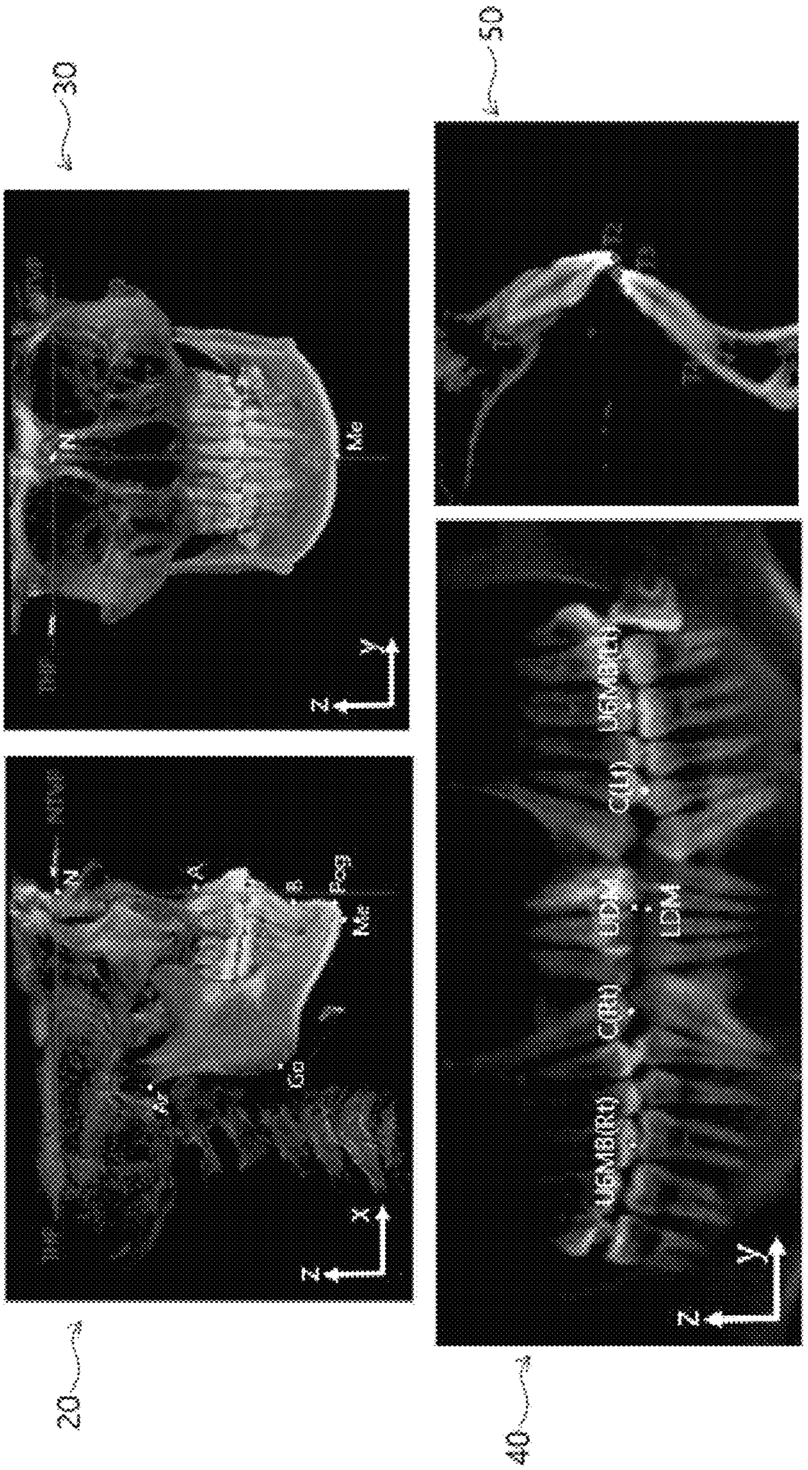
FIG. 3 illustrates positions of a plurality of cephalometric landmarks on an image of three-dimensional CBCT image for diagnosis.

FIG. 3 illustrates positions of a plurality of cephalometric landmarks for deriving 13 parameters on the CBCT image 20 in the sagittal plane, the CBCT image 30 in the coronal plane, the dental panoramic image 40, and the incisor image in a cross-sectional view 50.

As illustrated in FIG. 3, in step S200 of detecting the cephalometric landmarks, predetermined cephalometric landmarks may be automatically detected by the machine learning algorithm and image analysis processing technology to derive the 13 parameters from the CBCT image 20 in the sagittal plane, the CBCT image 30 in the coronal plane, and the dental panoramic image 40 obtained in step S100 after obtaining the 3D CBCT image for diagnosis based on the machine learning algorithm.

Here, in order to provide information on the orthodontic diagnosis with respect to the patient, a degree of protrusion of a maxilla, a degree of protrusion of a mandible, a degree of protrusion of chin, a degree of displacement of a mandible, a degree of displacement of the midline of upper central incisors, and a degree of displacement of the midline of lower central incisors, a vertical distance from the true horizontal plane (THP) passing through nasion (N), which is the most concave point between a frontal bone and a nasal bone, to the cusp tip of a right upper canine, a vertical distance from the THP to the cusp tip of a left upper canine, a vertical distance from the THP to the mesio-buccal cusp tip of a right upper first molars, a vertical distance from the THP to the mesio-buccal cusp tip of a left upper first molars, a degree of inclination of a upper central incisor, s degree of inclination of a lower central incisor, and s degree of inclination of the mandible with respect to the THP, may be derived as the 13 parameters.

To this end, the 13 parameters may be defined by keypoints of cephalometric landmarks corresponding to distances or angles between the detected a plurality of cephalometric landmarks from the 3D CBCT image for diagnosis, as shown in Table 1 below.

TABLE 1

| NUMBER | KEYPOINTS OF CEPHALOMETRIC LANDMARKS | PARAMETER |
|---|---|---|
| 1 | dx(A, NTVP) | DEGREE OF PROTRUSION OF MAXILLA |
| 2 | dx(B, NTVP) | DEGREE OF PROTRUSION OF MANDIBLE |
| 3 | dx(Pog, NTVP) | DEGREE OF PROTRUSION OF CHIN |
| 4 | dy(Me, NTVP) | DEGREE OF DISPLACEMENT OF CENTER OF MANDIBLE |
| 5 | dy(UDM, NTVP) | DEGREE OF DISPLACEMENT OF MIDLINE OF UPPER CENTRAL INCISORS |
| 6 | dy(LDM, NTVP) | DEGREE OF DISPLACEMENT OF MIDLINE OF LOWER CENTRAL INCISORS |
| 7 | dz(Ct(Rt),THP) | VERTICAL DISTANCE FROM THP TO THE CUSP TIP OF RIGHT UPPER CANINE |
| 8 | dz(Ct(Lt),THP) | VERTICAL DISTANCE FROM THP TO THE CUSP TIP OF LEFT UPPER CANINE |
| 9 | dz(U6MB(Rt), THP) | VERTICAL DISTANCE FROM THP TO THE MESIO-BUCCAL CUSP TIP OF RIGHT UPPER FIRST MOLARS |
| 10 | dz(U6MB(LT), THP) | VERTICAL DISTANCE FROM THP TO THE MESIO-BUCCAL CUSP TIP OF LEFT UPPER FIRST MOLARS |
| 11 | a($\overline{T_1T_2}$, THP) | DEGREE OF INCLINATION OF UPPER CENTRAL INCISOR |
| 12 | a($\overline{T_3T_4}$, MeGo) | DEGREE OF INCLINATION OF LOWER CENTRAL INCISOR |
| 13 | a(MeGo, THP) | DEGREE OF INCLINATION OF MANDIBLE WITH RESPECT TO THP |

With reference to FIG. 3 and Table 1, a plurality of cephalometric landmarks detected in each 3D CBCT image for diagnosis, the keypoints of the cephalometric landmarks corresponding to distances or angles between a plurality of cephalometric landmarks, and 13 parameters derived therefrom are described.

The machine learning algorithm may detect nasion (N) which is the most concave point between a frontal bone and a nasal bone in the CBCT image 20 in the sagittal plane, and A-point (A), which is the most concave point in the maxilla, and may diagnose the antero-posterior relationship of the maxilla and the mandible of the patient by deriving one of the 13 parameters, which is the degree of protrusion of the maxilla, through measuring a distance in the x-axis direction in the CBCT image 20 in the sagittal plane, between the nasion true vertical plane (NTVP), which is a vertical plane passing through nasion (N), and A-point (A).

In addition, the machine learning algorithm may detect nasion (N), which is the most concave point between a frontal bone and a nasal bone in the CBCT image 20 in the sagittal plane, and B-point (B), which is the most concave point in the mandible, and may diagnose the antero-posterior relationship of the maxilla and the mandible of the patient by deriving one of the 13 parameters, which is the degree of protrusion of the maxilla, through measuring a distance in the x-axis direction in the CBCT image 20 in the sagittal plane, between the nasion true vertical plane (NTVP), which is a vertical plane passing through nasion (N), and B-point (B).

In addition, the machine learning algorithm may detect nasion (N), which is the most concave point between a frontal bone and a nasal bone, and pogonion (Pog), which is the most prominent point on the chin, in the CBCT image 20 in the sagittal plane, and may diagnose the antero-posterior relationship of the maxilla and the mandible of the patient by deriving one of the 13 parameters, which is the degree of protrusion of the chin, through measuring a distance in the x-axis direction in the CBCT image 20 in the sagittal plane, between the nasion true vertical plane (NTVP), which is a vertical plane passing through nasion (N), and pogonion (Pog).

In addition, the machine learning algorithm may detect nasion (N), which is the most concave point between a frontal bone and a nasal bone in the CBCT image 30 in the coronal plane, and menton (Me), which is the lowest point of the mandible, and may diagnose the left-right occlusal relationship of the patient's maxilla and mandible by deriving the degree of displacement of the center of the mandible, which is one of the 13 parameters, through measuring a distance in the y-axis direction in the CBCT image 30 in the coronal plane between the nasion true vertical plane (NTVP), which is a vertical plane passing through nasion (N), and menton (Me).

In addition, the machine learning algorithm may detect nasion (N), which is the most concave point between a frontal bone and a nasal bone extracted from the CBCT image 30 in the coronal plane, and a vertical line passing through the midline of the upper central incisors (Upper dental midline; UDM) in the dental panoramic image 40, and may diagnose the left-right occlusal relationship of the patient's maxilla and mandible by deriving the degree of displacement of the midline of the upper central incisors, which is one of the 13 parameters, through measuring a distance in the y-axis direction in the CBCT image in the coronal plane between the nasion true vertical plane (NTVP), which is a vertical plane passing through nasion (N), and a vertical line passing through the center of the upper central incisors (UDM).

In addition, the machine learning algorithm may detect nasion (N), which is the most concave point between a frontal bone and a nasal bone extracted from the CBCT image 30 in the coronal plane, and a vertical line passing through the midline of the lower central incisors (Lower dental midline; LDM) in the dental panoramic image 40, and may diagnose the left and right occlusal relationship of the patient's maxilla and mandible by deriving the degree of displacement of the midline of the lower central incisors, which is one of the 13 parameters, through measuring a distance in the y-axis direction in the CBCT image in the coronal plane, between a vertical plane passing through nasion (N) and a vertical line passing through the center of the lower central incisors (LDM).

In addition, the machine learning algorithm may detect nasion (N), which is the most concave point between a frontal bone and a nasal bone extracted from the CBCT image 30 in the coronal plane, and the cusp tip of the right upper canine (Ct (Rt)) in the dental panoramic image 40. A vertical distance between the true horizontal plane (THP), which is a horizontal plane passing through nasion (N), and the cusp tip of the upper right canine (Ct (Rt)) is derived as one of the 13 parameters, so that the machine learning algorithm may identify a distance between the horizontal plane and the right upper canine.

In addition, the machine learning algorithm may detect nasion (N), which is the most concave point between a frontal bone and a nasal bone extracted from the CBCT image 30 in the coronal plane, and the cusp tip of the left upper canine (Ct (Lt)) in the dental panoramic image 40. A vertical distance in the z-axis direction between the true horizontal plane (THP), which is a horizontal plane passing through nasion (N), and the cusp tip of the left upper canine (Ct (Lt)) in the CBCT image 30 in the coronal plane is derived as one of the 13 parameters, so that the machine learning algorithm may identify a distance between the horizontal plane and the left upper canine.

As a result, the distances to the right and left upper canines measured in the horizontal plane should match each other, but when there is a discrepancy therebetween, it can be seen that the maxilla is inclined in the canine portion.

In addition, the machine learning algorithm may detect nasion (N), which is the most concave point between a frontal bone and a nasal bone extracted from the CBCT image 30 in the coronal plane, and the mesio-busccal cusp tip of the right upper first molar (U6 MB (Rt)) in the dental panoramic image 40. A vertical distance between the true horizontal plane (THP), which is a horizontal plane passing through nasion, and the right upper first molar (U6 MB (Rt)) is derived as one of the 13 parameters, so that the machine learning algorithm may identify a distance between the horizontal plane and the right upper first molar.

In addition, the machine learning algorithm may detect nasion (N), which is the most concave point between a frontal bone and a nasal bone extracted from the CBCT image 30 in the coronal plane, and the mesio-buccal cusp tip of the left upper first molar (U6 MB (Lt)) in the dental panoramic image 40. A vertical distance between the true horizontal plane (THP), which is a horizontal plane passing through nasion (N), and the left upper first molar (U6 MB (Lt)) is derived as one of the 13 parameters, so that the machine learning algorithm may identify a distance between the horizontal plane and the left upper first molar.

As a result, the distances to the right upper first molar and the left upper first molar measured in the horizontal plane should match each other, but when there is a discrepancy therebetween, it can be seen that the maxilla is inclined in the molar portion.

In addition, the machine learning algorithm may detect nasion (N), which is the most concave point between a frontal bone and a nasal bone extracted from the CBCT image 30 in the sagittal plane, and the crown tip T1 and the root tip T2 of the upper incisor in the incisor image in a cross-sectional view 50. The degree of inclination of the upper central incisor is derived as one of the 13 parameters through an angle of the true horizontal plane (THP), which is a horizontal plane passing through nasion (N), and a vector connecting the crown tip T1 and the root tip T2 of the upper central incisor, so that the machine learning algorithm may diagnose the occlusal state of the patient.

In addition, the machine learning algorithm may detect menton (Me), which is the lowest point in the mandible, and gonion (Go), which is a point of maximum curvature in the mandibular angle, in the CBCT image 30 in the sagittal plane, and the crown tip T3 of the lower incisor and the root tip T4 of the lower incisor in the incisor image in a cross-sectional view 50, respectively. The degree of inclination of the lower central incisor is derived as one of the 13 parameters through an angle of a MeGo line connecting menton (Me) and the gonion (Go) and a vector connecting the the crown tip T3 of the lower incisor and the root tip T4 of the lower incisor, so that the machine learning algorithm may diagnose the occlusal state of the patient.

In addition, the machine learning algorithm may detect nasion (N), which is the most concave point between a frontal bone and a nasal bone, menton (Me), which is the lowest point on the mandible, and the gonion (Go), which is the point of maximum curvature on the mandibular angle, in the CBCT image 20 in the sagittal plane. The degree of inclination of the mandible with respect to the true horizontal plane (THP), which is a horizontal plane passing through nasion (N) is derived as one of the 13 parameters through an angle between the true horizontal plane (THP) and the MeGo line connecting menton (Me) and the gonion (Go), so that the machine learning algorithm may diagnose the patient's vertical mandibular and maxillary relationship.

Figure 4:
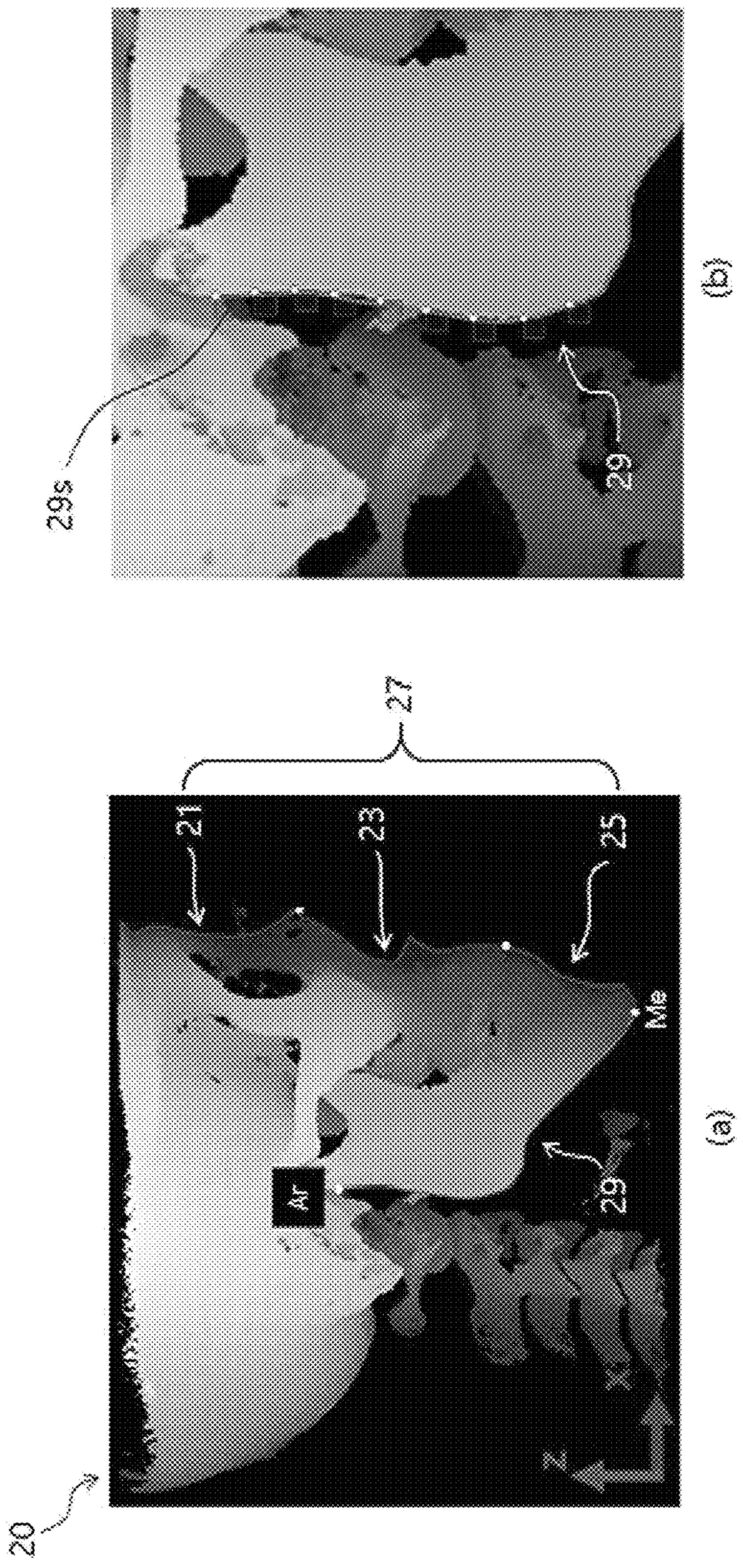
FIG. 4 illustrates a process of detecting a plurality of cephalometric landmarks on a CBCT image in a sagittal plane through machine learning algorithm.

FIG. 4 illustrates a process of detecting a plurality of cephalometric landmarks for deriving the parameters in the CBCT image in the sagittal plane through machine learning algorithm.

As illustrated in FIG. 4A, the machine learning algorithm may divide the CBCT image 20 of the patient in the sagittal plane into four regions of interest (ROIs) to detect a plurality of cephalometric landmarks. Here, the CBCT image 20 in the sagittal plane may be divided into a first region 21 provided between a frontal bone portion and nasion positioned at a lowermost position where two nasal bones meet, a second region 23 provided between nasion and the upper teeth, a third region 25 provided between the lower teeth and the lowest point of the mandible (menton), and a fourth region 29 provided between the lowest point of the mandible (menton, Me) and an articular bone of jaw (Ar). A plurality of cephalometric landmarks for deriving the parameters may be detected in each of the four regions of interest.

To this end, the machine learning algorithm may, in order to divide the CBCT image 20 in the sagittal plane into each of the four regions of interest, divide the CBCT image 20 in the sagittal plane into a facial portion profile region 27, which is indicated by a red line along the front of the patient's facial portion and configured with the first region 21, the second region 23, and the third region 25, and a jaw profile region 27, which is indicated by a green line along the patient's mandible region and configured with the fourth region 25, and may extract the facial portion profile region 27 and the jaw profile region 27. The CBCT image 20 in the sagittal plane may be divided into a plurality of unit pixels that are horizontal or vertical to the y-axis direction, respectively, for extraction of the facial portion profile region 27 and the jaw profile region configured with the fourth region 29 from the CBCT image 20 in the sagittal plane.

As illustrated in FIG. 4A, the process extracting the patient's facial portion profile region 27 from the CBCT image 20 in the sagittal plane may be performed based on the similarity to other neighboring pixels at any point within the CBCT image 20 in the sagittal plane in terms of the degree of depth and a characteristic as a skull boundary. Specifically, a coordinate value D (xi, i) of a unit pixel having the largest non-zero x-axis value in the CBCT image 20 in the sagittal plane may be considered to be present in the facial portion profile region 27 when the coordinate value D (xi, i) satisfies the following expression compared to a unit pixel positioned in the previous row (i-1).

$$\begin{cases} D(x'i, i) > 0, \forall i = 2, \ldots, n \\ |D(x'i, i) - D(xi-1, i-1)| < d \\ |xi - xi - 1)| = \min|x'i - xi - 1)|, \forall x'i \end{cases}$$

Here, n is the number of pixels divided in the y-axis direction in the CBCT image in the sagittal plane.

Next, based on the facial portion profile region 27 obtained from the CBCT image 20 in the sagittal plane, menton (Me) is designated as a starting point to extract the jaw profile region including the fourth region 29. As illustrated in FIG. 4B, after the jaw profile region configured with the fourth region 29 in the CBCT image in the sagittal plane is divided into a plurality of regions of interest 29*s*, the degree of average depth in each of a plurality of regions of interest 29*s* is calculated, and the articular bone of jaw (Ar) may be detected by measuring an actual distance between the degree of depth in a region of interest in which the degree of average depth changes rapidly and a vertical plane of the skull.

With reference to FIGS. 3 and 4, the machine learning algorithm may detect a lowest positioned point along the x-axis direction in the first region 21 constituting the CBCT image 20 in the direction of the sagittal plane as nasion (N), recognize a vertical plane extending along the z-axis direction passing through the detected nasion N as the nasion true vertical plane (NTVP), and recognize a horizontal line extending along the y-axis direction passing through nasion (N) as the true horizontal plane (THP) to derive the parameters.

In addition, the machine learning algorithm may detect the root tip of the upper incisor portion in the second region 23 constituting the CBCT image 20 in the sagittal plane as A-point (A). Meanwhile, when the machine learning algorithm has difficulty in recognizing the shape of the upper incisor portion within the second region 23 constituting the CBCT image in the sagittal plane, the shape of the upper incisor portion may be supplemented by gently connecting a boundary region between an acanthion provided in an upper portion of the upper incisor portion and protruding forward to the teeth and the upper incisor portion. Then, the machine learning algorithm may detect a point that is at the lowest position in the x-axis direction within a facial portion profile boundary region, or the point that has the smallest slope within the facial portion profile boundary region, as A-point (A).

In addition, the machine learning algorithm may detect B-point (B), which is the lowest point in the x-axis direction in the mandible, pogonion (Pog), which is the highest point in the x-axis direction in the mandible, and menton (Me), which is the lowest point in the y-axis direction in the mandible, respectively, in the third region 25 constituting the CBCT image 20 in the sagittal plane.

Meanwhile, when the mandible of the patient is recessed inwardly relative to the lower incisor portion, B-point (B) and pogonion (Pog) may not be smoothly detected by the method described above, in which case the machine learning algorithm may detect the most concave point and the most prominent point of the mandible as B-point B and pogonion (Pog), respectively, in the third region 25 constituting the CBCT image 20 in the sagittal plane.

In addition, the machine learning algorithm may detect gonion (Go), which is the point of maximum curvature of the mandibular angle, in the fourth region 29 constituting the CBCT image 20 in the sagittal plane. To this end, the machine learning algorithm may detect an intersecting point of a tangent line that passes through menton (Me) and is tangent to the lower portion of the mandible, and the tangent line that passes through the articular bone of jaw (Ar) and is tangent to a left sided portion of the mandible, as gonion (Go).

Figure 5:
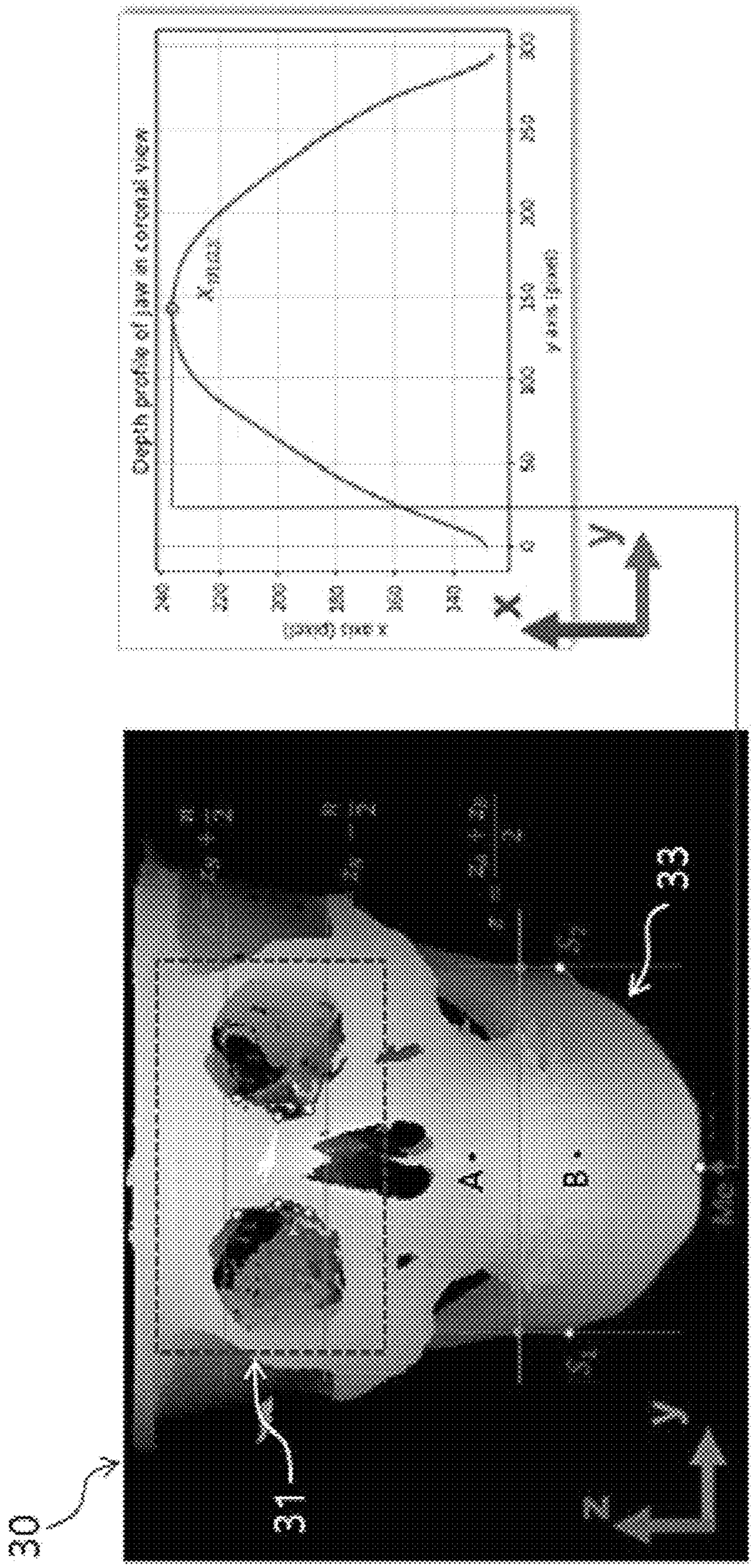
FIG. 5 illustrates a process of detecting a plurality of cephalometric landmarks on a CBCT image in a coronal plane using the machine learning algorithm.

FIG. 5 illustrates a process of detecting a plurality of cephalometric landmarks on the CBCT image in the direction of the coronal plane using the machine learning algorithm.

As illustrated in FIG. 5, the machine learning algorithm may divide the CBCT image 30 in the coronal plane such that two regions of interest (ROIs) are included to detect a plurality of cephalometric landmarks. The machine learning algorithm may divide the CBCT image 30 in the coronal plane into a fifth region 31, which is included in the facial portion between the nasion and the eyes, and a sixth region 33, which is the mandible region, to detect the cephalometric landmarks for the cephalometric measurements, respectively.

Meanwhile, since each nasion (N) detected in the CBCT image 30 in the coronal plane and the CBCT image 20 in the sagittal plane shares the same z-axis position coordinate, the y-axis position coordinate in the CBCT image 30 in the coronal plane may serve as a major factor in the process of detecting nasion (N). In the CBCT image 20 in the coronal plane, the y-axis position coordinate $y_N$ of nasion (N) may be detected by the following expression 2 by detecting a left end coordinate value $T_i$ and a right end coordinate value $T_i'$, in the nasal bone region from a plurality of unit pixels included between $$Z_n - \frac{n}{2} \text{ and } Z_n + \frac{n}{2}$$

(where $Z_N$ is the z-axis position coordinate of an N point, and n is a natural number).

$$y_N = \frac{\sum_{i^n} \left( \frac{y_{Ti} + y_{T'i}}{2} \right)}{n} \quad \text{[Expression 2]}$$

In the process of detecting the sixth region 33 in the CBCT image 30 in the coronal plane, the machine learning algorithm detects an intersection points $S_1$ and $S_2$ where a vertical line passing through a z-axis position coordinate ($Z_A$) of A-point (A) and a z-axis position coordinate $$\left( Z = \frac{Z_A + Z_B}{2} \right)$$

of a midpoint of the z-axis position coordinate (ZB) of B-point (B), which are detected in the CBCT image 20 in the sagittal plane, meets the left mandible and the right mandible of the CBCT image 30 in the coronal plane, respectively, and the machine learning algorithm may designate a region below the detected pair of intersection points $S_1$ and $S_2$ as the sixth region 33 in the CBCT image 30 in the coronal plane.

Further, the machine learning algorithm may detect a region of a convex shape in the z-axis direction in the sixth region 33 of the CBCT image 30 in the coronal plane, and detect a point with the largest x-axis coordinate value in the region as menton (Me).

FIGS. 6 to 10 illustrate a process detecting a plurality of cephalometric landmarks on a dental panoramic image using the machine learning algorithm.

Figure 6:
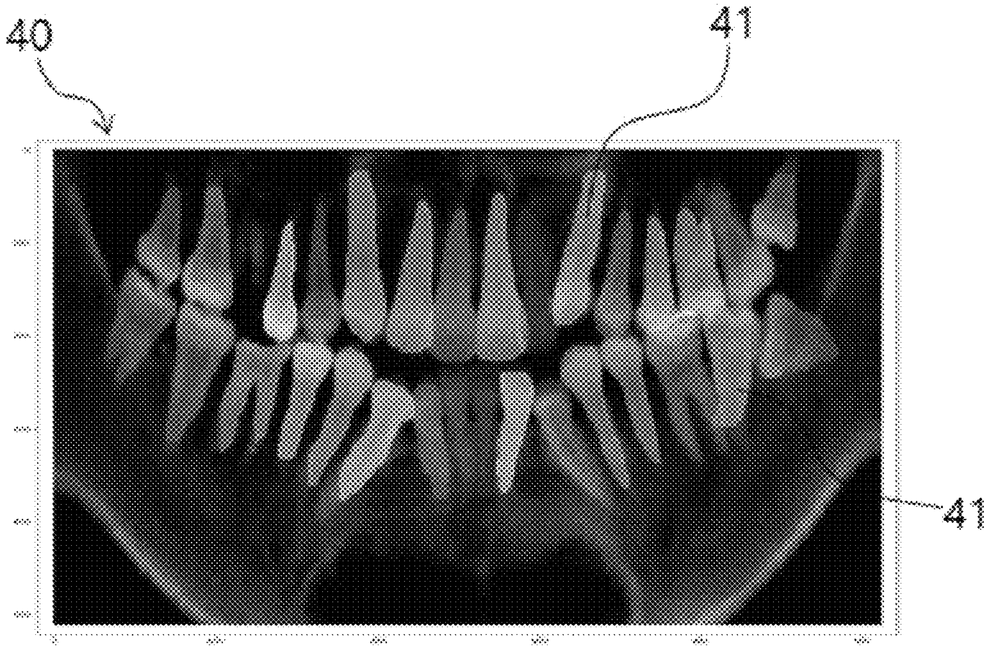
FIGS. 6 to 10 illustrate a process of detecting a plurality of cephalometric landmarks on a dental panoramic image using the machine learning algorithm.

FIG. 6 illustrates a process detecting each individual tooth region 41 from the entire set of teeth of a patient by applying a region based convolutional neural network (R-CNN) machine learning model on the dental panoramic image 40 on the basis of the machine learning algorithm. The individual tooth region 41 may be represented by a plurality of different colors to be distinguished from neighboring regions.

Figure 7:
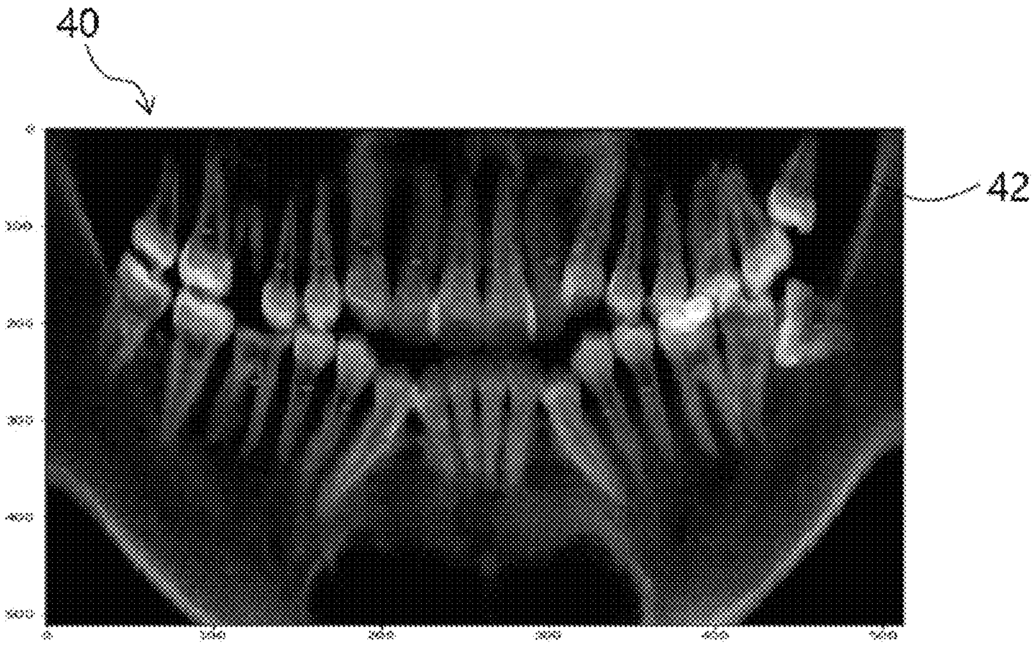

FIG. 7 illustrates a process for detecting a teeth landmark 42 indicating a position of a tooth for each individual tooth region 41 in the detected entire set of teeth. Here, the teeth landmark 42 may be detected as a midpoint inside each individual tooth region 41 in the entire set of teeth detected from a Mask R-CNN model.

Figure 8:
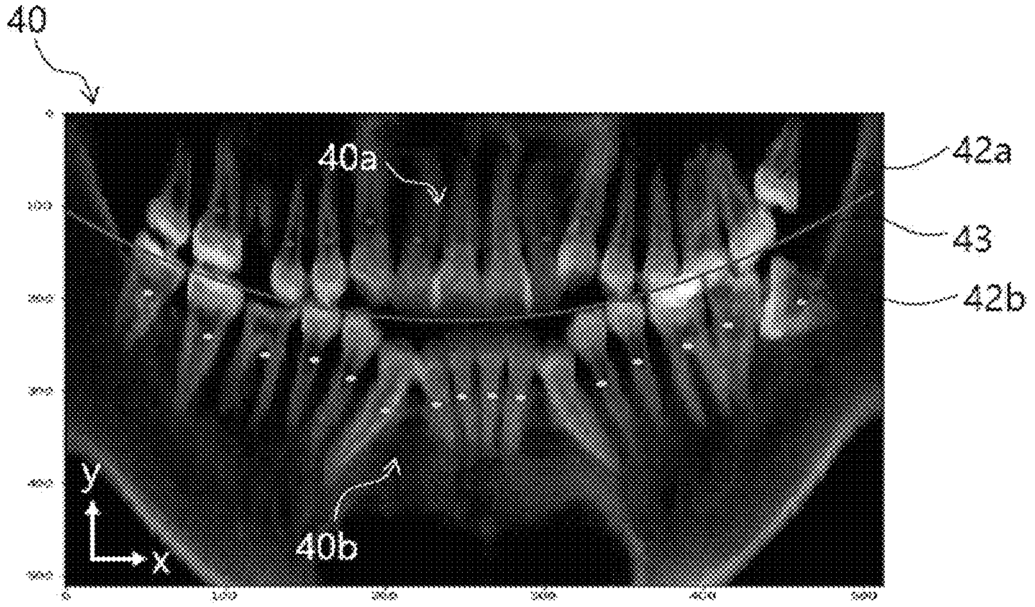

FIG. 8 illustrates a process of classifying the entire set of teeth of the patient in the dental panoramic image 40 into upper teeth **40*a* and lower teeth 40*b* by analyzing the positions of the detected teeth landmarks 42**.

As a statistical technique for the classification above, a two-dimensional position coordinate corresponding to each of the positions of the detected plurality of teeth landmarks 42 may be set according to a linear regression method, and a quadratic function 43 passing through the coordinates may be generated. The teeth landmarks 42 may be divided into upper teeth landmarks **42*a* and lower teeth landmarks 42*b* by detecting the position of the detected teeth landmarks 42 in FIG. 7 and the relative position of the quadratic function 43. Therefore, the entire set of teeth appearing in the dental panoramic image 40 may be classified as the upper teeth 40*a* or the lower teeth 40*b***.

Figure 9:
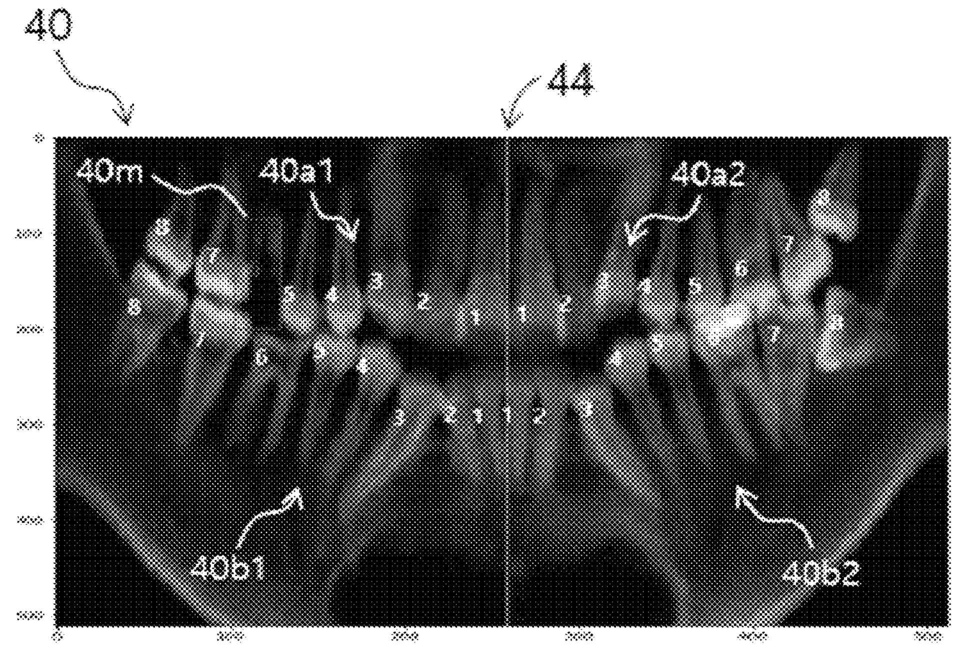

FIG. 9 illustrates a process of numbering right upper teeth **40*a*1, left upper teeth 40*a*2, right lower teeth 40*b*1, and left lower teeth 40*b*2, respectively, through the calculation of distances to the teeth landmarks 42 detected on each of the upper teeth 40*a* and the lower teeth 40*b*, based on a horizontal distance from the midline 44 of the facial portion in the dental panoramic image 40**.

Through the numbering process above, the entire set of teeth of the patient appearing in the dental panoramic image 40 may be numbered sequentially in order of shortest horizontal distance from the midline 44 of the facial portion to the detected cephalometric landmarks 42 (see FIG. 8).

In addition, through the numbering process above, a missing tooth **40*m* may be detected by detecting an abnormal deviation in the distance from the midline 44 of the facial portion to the teeth landmarks detected on each of two neighboring teeth. In the embodiment in FIG. 9, the machine learning algorithm may identify that a first molar (tooth 6) of the right upper teeth 40*a*1 is the missing tooth 40*m***.

Figure 10:
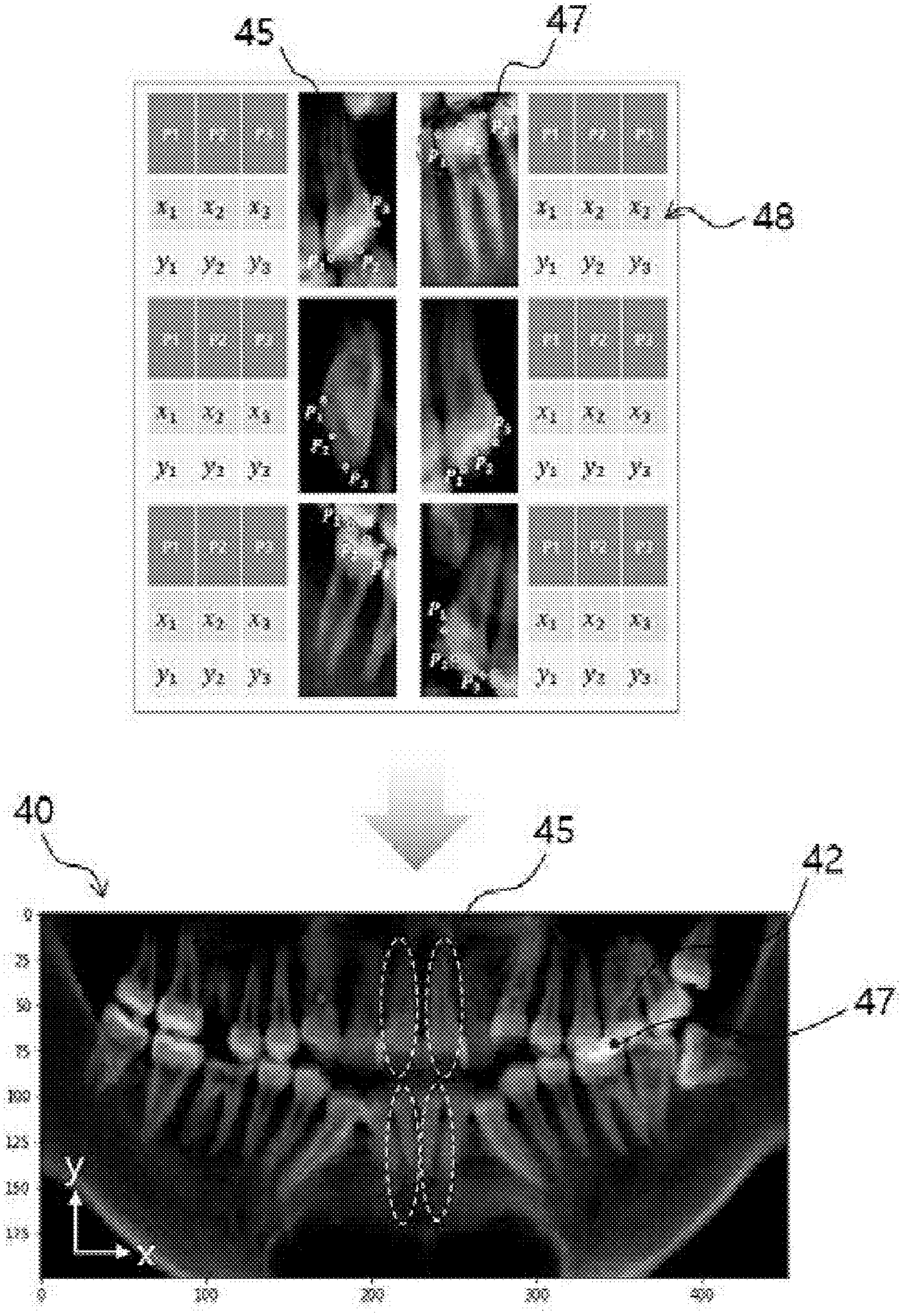

FIG. 10 illustrates a process of analyzing the numbered teeth to detect a plurality of cephalometric landmarks for deriving parameters from the teeth to be detected, including an incisor, a canine, and a first molar, among the entire set of teeth appearing in the dental panoramic image 40.

With reference to FIG. 9, the teeth 45 to be detected, whose cephalometric landmarks are required to be detected in order to derive the 13 parameters are an incisor (tooth 1), a canine (tooth 3), and a first molar (tooth 6) in the right upper teeth **40*a*1, an incisor (tooth 1), a canine (tooth 3), and a first molar (tooth 6) in the left upper teeth 40*a*2, an incisor (tooth 1) in the right lower teeth 40*b*1, and an incisor (tooth 1) in the left lower teeth 40*a*2, among the entire set of teeth appearing in the dental panoramic image 40**.

As illustrated in FIG. 10, the machine learning algorithm may detect three teeth landmarks 47 at each of a plurality of teeth 45 to be detected by adjusting a size of a region of interest (ROI) that includes the plurality of teeth 45 to be detected, including the aforementioned incisor, canine, and first molar, and loading the adjusted region of interest for the plurality of teeth 45 to be detected into the CNN model.

Here, the three teeth landmarks 47 detected at each of a plurality of teeth 45 to be detected are configured with a left teeth landmark $P_1$, a center teeth landmark $P_2$, and a right teeth landmark $P_3$ in a tooth enamel site of a dental crown constituting the tooth. Consequently, a plurality of cephalometric landmarks may be detected in the dental panoramic image 40 for deriving the parameters from each of the teeth 45 to be detected based on position coordinates 48 for each of the three teeth landmarks detected from the teeth 45 to be detected that have been trained from the CNN model.

For example, the machine learning algorithm may define a midpoint of the center teeth landmark $P_2$ as a midpoint of the upper central incisor (UDM) and a midpoint of the lower central incisor (LDM) among the three cephalometric landmarks detected on each of the upper incisor and the lower incisor in the dental panoramic image 40 illustrated in FIG. 10 in order to detect a plurality of cephalometric landmarks for deriving the parameters.

Meanwhile, the three teeth landmarks $P_1$, $P_2$, and $P_3$ are detected from each of the four anterior teeth 45 detected through the dental panoramic image 40, and the incisor image in a cross-sectional view 50 may be obtained from the dental panoramic image 40 based on the three teeth landmarks $P_1$, $P_2$, and $P_3$ detected from each of the four anterior teeth 45 (see FIG. 3). With reference to FIG. 3, the machine learning algorithm may precisely detect the crown tip $T_1$ of the upper incisor, the root tip $T_2$ of the upper incisor, the crown tip $T_3$ of the lower incisor, and the root tip $T_4$ of the lower incisor in the incisor image in a cross-sectional view 50 using CNN model distributed processing.

The machine learning algorithm may measure the angle between the vector connecting the crown tip $T_1$ and the root tip $T_2$ of the upper incisor detected on the incisor image in a cross-sectional view and the horizontal plane (NTVP) passing through the N point, and measure the angle between the vector connecting the crown tip $T_3$ and the root tip $T_4$ of the lower incisor and the MeGo line, consequently to evaluate the degree of inclination of the anterior teeth portion and use the degree of inclination as the parameter for orthodontic diagnosis.

As described above, the method deriving cephalometric parameters for orthodontic diagnosis based on machine learning according to the present invention may further include a step S400 diagnosing the facial profile of the patient or occlusal state corresponding to the 13 parameters derived in step S300 deriving the 13 parameters.

Here, when the patient's occlusal state is diagnosed in correspondence with the 13 parameters, the machine learning algorithm may diagnose the patient's occlusal state by classifying the occlusal state into a state in which the antero-posterior relationship of the maxilla and the mandible is in a relatively normal category, a state in which the maxilla is relatively protruding compared to the mandible, and a state in which the mandible is relatively protruding compared to the maxilla, respectively, according to an internally stored reference value of the parameter in order to distinguish between a normal occlusion and a malocclusion.

Further, when the facial profile of the patient is diagnosed in correspondence with the derived 13 parameters, the machine learning algorithm may diagnose the facial profile of the patient by classifying the facial profile of the patient into a state in which a length of the facial portion is in a normal category, a state in which the length of the facial portion is shorter than the normal category, and a state in which the length of the facial portion is longer than the normal category according to the internally stored reference value of the parameter in order to analyze the length of the patient's facial portion to perform the correction diagnosis.

Figure 11:
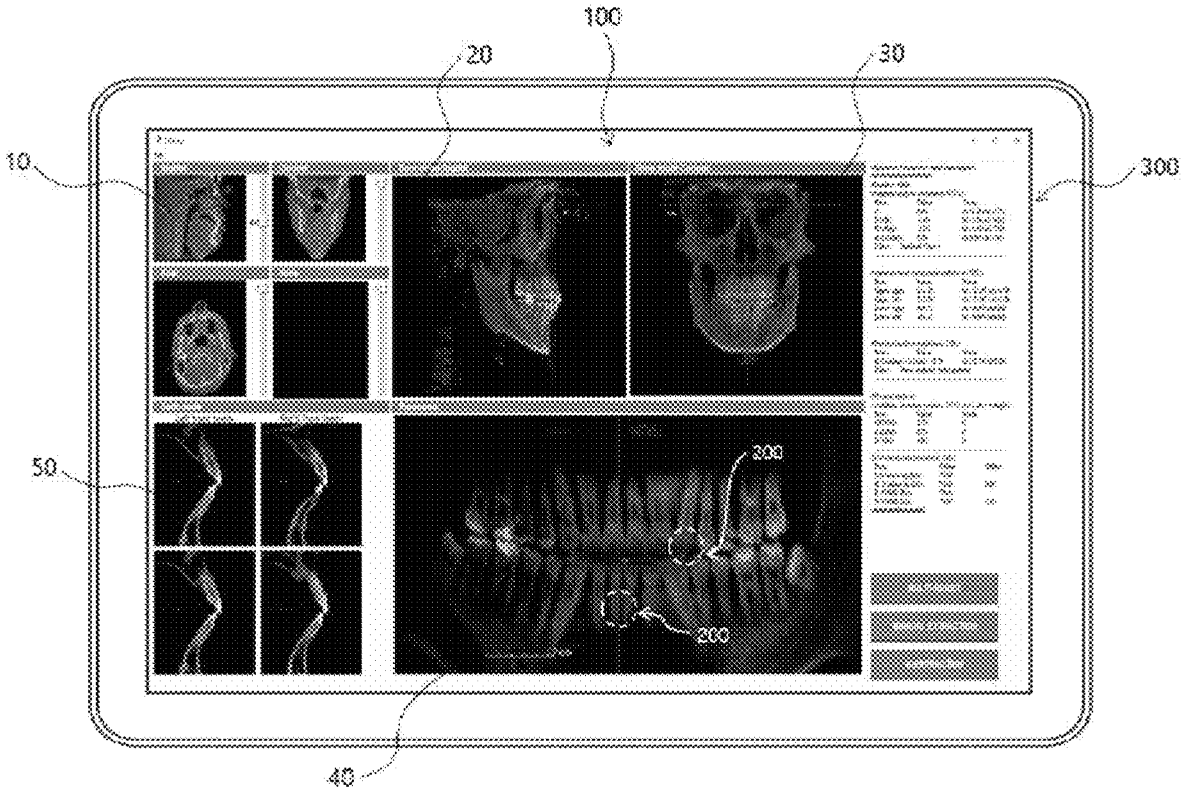

FIG. 11 illustrates a screen of a graphic user interface to which the method deriving cephalometric parameters based on machine learning according to the present invention is applied, and FIG. 12 is an enlarged view illustrating a display area of a diagnosis result on the screen of the graphic user interface illustrated in FIG. 11.

The graphic user interface (GUI) to which the method deriving cephalometric parameters based on machine learning illustrated in FIG. 11 may display a plurality of images, input/output icons, or the like that represent a process executing each step of the method deriving cephalometric parameters based on machine learning on the display screen of the display whenever each step constituting the method deriving cephalometric parameters based on machine learning is executed.

For example, when step S100 obtaining the 3D CBCT image for diagnosis is executed in the method deriving cephalometric parameters based on machine learning, a plurality of 3D CBCT images for diagnosis, including the cone beam computed tomography (CBCT) image data 10 of the facial portion of the patient through a 3D CBCT image generation area 100, and the CBCT image 20 in the sagittal plane, the CBCT image 30 in the coronal plane, the dental panoramic image 40, and the incisor image in a cross-sectional view 50 that are extracted from the CBCT image data 10, may appear on the display screen.

Further, when step S200 detecting a plurality of cephalometric landmarks on the method deriving cephalometric parameters based on machine learning is executed, the cephalometric landmarks for deriving the parameters are automatically detected by the machine learning algorithm of the present invention in a cephalometric landmarks display area 200, or icons such as various symbols, shapes, and the like corresponding to the detected cephalometric landmarks may appear on the display screen to allow a skilled person, such as a dentist, to display the cephalometric landmarks that the skilled person manually and directly detects on the display screen.

As illustrated in FIG. 12, when step S200 detecting a plurality of cephalometric landmarks is performed in the method deriving cephalometric parameters based on machine learning, information 310 on the derived 13 parameters may be displayed through a diagnosis result display area 300 appearing on the display screen after step S300 deriving the 13 parameters by the machine learning algorithm input to a processor constituting the user graphic interface (GUI) device is performed.

Meanwhile, it has been described above that the method deriving cephalometric parameters based on machine learning according to the present invention may further include step S400 diagnosing the facial profile of the patient or occlusal state in correspondence with the 13 parameters that have been derived in step S300 deriving the 13 parameters.

Accordingly, when step S400 diagnosing the facial profile of the patient or occlusal state in the method deriving cephalometric parameters for orthodontic diagnosis based on machine learning is executed, information 320 that the occlusal state or the facial profile of the patient has been automatically diagnosed in correspondence with the 13 parameters may be displayed on the display screen through the diagnosis result display area 300.

For example, when the antero-posterior position of mandible and maxilla of the patient is in the relatively normal category, the diagnosis information may be represented as "Class I", when the maxilla of the patient is in a state of relatively protrusion compared to the mandible, the diagnosis information may be represented as "Class II", and when the mandible is in a state of relatively protrusion compared to the maxilla, the diagnosis information may be represented as "Class III", and the like.

In addition, information 320 on the facial profile of the patient may be displayed as the diagnosis result 300 on the display area of display screen, such as a phrase such as "Meso-cephalic facial pattern" for a state in which the length of the patient's facial portion is in the normal category, "Brachy-cephalic facial pattern" for a state in which the length of the patient's facial portion is shorter than the normal category, and "Dolicho-cephalic facial pattern" for a state in which the length of the patient's facial portion is longer than the normal category.

This method deriving cephalometric parameters may be programmed in a program for deriving cephalometric parameters and installed or stored on a user computing device or a computable cloud server. Such a program may be programmed to automatically perform a step detecting a plurality of cephalometric landmarks as output data and a step deriving 13 parameters corresponding to the distances or angles between the detected plurality of cephalometric landmarks, using the 3D CBCT image for diagnosis extracted after the step obtaining the 3D CBCT image for diagnosis of the aforementioned method deriving cephalometric parameters as input data.

Of course, the program for deriving cephalometric parameters may be programmed such that the step detecting a plurality of cephalometric landmarks as output data and the step of deriving 13 parameters corresponding to the distances or angles between the detected cephalometric landmarks are performed sequentially or step by step according to the user's selection.

As described above, in the method deriving cephalometric parameters based on machine learning according to the present invention, the 3D CBCT image for diagnosis extracted from a specific angle is obtained from the image data captured by the CBCT for a patient with the machine learning algorithm being applied, and the entire process of deriving 13 parameters corresponding to a plurality of cephalometric landmarks detected from the 3D CBCT image for diagnosis can be performed within a few seconds to tens of seconds, so that the derivation of parameters for orthodontic diagnosis can be performed quickly and consistently with high accuracy.

Further, when the method deriving cephalometric parameters based on machine learning according to the present invention is combined with a graphic user interface, the results performed in each step of the method are displayed on a display screen, so that a third party such as a patient and a dentist can smoothly grasp the process deriving cephalometric landmarks and 13 parameters for orthodontic diagnosis and the diagnosis results.

Furthermore, the method deriving cephalometric parameters based on machine learning according to the present invention has an excellent expected effect further expanding the scope of application such as automatically designing a customized dental orthodontic device for a patient in correspondence with the derived 13 parameters, from the effect automatically diagnosing and indicating the facial profile or occlusal state of the patient.

While the present invention has been described above with reference to the exemplary embodiments, it may be understood by those skilled in the art that the present invention may be variously modified and changed without departing from the spirit and scope of the present invention disclosed in the claims. Therefore, it should be understood that any modified embodiment that essentially includes the constituent elements of the claims of the present invention is included in the technical scope of the present invention.

The invention claimed is:

1. A method of deriving cephalometric parameters for orthodontic diagnosis based on machine learning, the method comprising:

obtaining 3D cone beam computed tomography (CBCT) images for orthodontic diagnosis including a CBCT image in a sagittal plane, a CBCT image in a coronal plane, a dental panoramic image, and an incisor image in a cross-sectional view, respectively, for a patient from 3D CBCT image data captured of the patient's head at a natural head position;

detecting, based on a machine learning algorithm, a plurality of cephalometric landmarks on the 3D CBCT images to derive 13 parameters for orthodontic diagnosis; and deriving 13 parameters corresponding to distances or angles between the detected plurality of cephalometric landmarks, wherein at least one of the 13 parameters is derived using one of a nasion true vertical plane (NTVP) and a true horizontal plane (THP) among the plurality of cephalometric landmarks, wherein the NTVP is a vertical plane passing through a nasion, the THP is a horizontal plane passing through the nasion, and the nasion is a most concave point between a frontal bone and a nasal bone.

2. The method of claim 1, wherein, in order to provide information on the orthodontic diagnosis, the 13 parameters include a degree of protrusion of a maxilla, a degree of protrusion of a mandible, a degree of protrusion of a chin, a degree of displacement of a center of a mandible, a degree of displacement of the midline of upper central incisors, a degree of displacement of the midline of lower central incisors, a vertical distance from the THP to a tip of a right upper canine, a vertical distance from the THP to a tip of a left upper canine, a vertical distance from the THP to a right upper first molars, a vertical distance from the THP to a left upper first molars, a degree of inclination of a upper central incisor, a degree of inclination of a lower central incisor, and a degree of inclination of the mandible with respect to the THP.

3. The method of claim 1, wherein the machine learning algorithm includes:

applying a region based convolutional neural network (R-CNN) machine learning model to the dental panoramic image to detect individual regions of entire set of teeth;

detecting, for each detected individual region of the entire set of teeth, teeth landmarks representing positions of the teeth;

analyzing the positions of the detected teeth landmarks to classify the entire set of teeth into upper teeth and lower teeth;

numbering each of right upper teeth, left upper teeth, right lower teeth, and left lower teeth sequentially based on a horizontal distance from the midline of a facial portion to the detected teeth landmarks; and analyzing the numbered teeth to detect a plurality of cephalometric landmarks for deriving a parameter from a specific tooth, including an incisor, a canine, and a first molar.

4. The method of claim 2, wherein the machine learning algorithm detects the nasion and an A-point-(A), which is a deepest portion of a line connecting an anterior nasal spine in the maxilla and a prosthion, in the CBCT image in the sagittal plane, and wherein the degree of protrusion of a maxilla is derived by measuring a distance between the NTVP and the A-point.

5. The method of claim 2, wherein the machine learning algorithm detects the nasion and a B-point, which is a deepest portion connecting an infradentale and a pogonion, which is a most prominent point of the chin, in the CBCT image in the sagittal plane, and wherein the degree of protrusion of the mandible is derived by measuring a distance between the NTVP and the B-point.

6. The method of claim 2, wherein the machine learning algorithm detects the nasion and a pogonion, which is a most prominent point of the chin, in the CBCT image in the sagittal plane, and wherein the degree of protrusion of the chin is derived by measuring a distance between the NTVP and the pogonion.

7. The method of claim 2, wherein the machine learning algorithm detects the nasion and a menton, which is a lowest point of the mandible, in the CBCT image in the coronal plane, and wherein the degree of displacement of a center of the mandible is derived by measuring a distance between the NTVP and the menton.

8. The method of claim 2, wherein the machine learning algorithm detects the nasion in the CBCT image in the coronal plane, and a midpoint of upper central incisors in the dental panoramic image, and wherein the degree of displacement of the midline of the upper central incisors is derived by measuring a distance between the NTVP and the midpoint of the upper central incisors.

9. The method of claim 2, wherein the machine learning algorithm detects the nasion in the CBCT image in the coronal plane, and a central point of lower central incisors in the dental panoramic image, and wherein the degree of displacement of the midline of the lower central incisors is derived by measuring a distance between the NTVP and the midpoint of the lower central incisors.

10. The method of claim 2, wherein the machine learning algorithm detects the nasion in the CBCT image in the coronal plane, and the cusp tip of the right upper canine in the dental panoramic image, and wherein the vertical distance between the THP and the cusp tip of the right upper canine is derived.

11. The method of claim 2, wherein the machine learning algorithm detects the nasion in the CBCT image in the coronal plane, and the cusp tip of the left upper canine in the dental panoramic image, and wherein the vertical distance between the THP and the cusp tip of the left upper canine is derived.

12. The method of claim 2, wherein the machine learning algorithm detects the nasion in the CBCT image in the coronal plane, and the mesio-buccal cusp tip of a right upper first molar in the dental panoramic image, and wherein, through a distance between the THP and the mesio-buccal cusp tip of the right upper first molar, the vertical distance from the THP to the right upper first molars is derived.

13. The method of claim 2, wherein the machine learning algorithm detects the nasion in the CBCT image in the coronal plane, and the mesio-buccal cusp tip of a left upper first molar in the dental panoramic image, and wherein, through a distance between the THP and the mesio-buccal cusp tip of the left upper first molar, the vertical distance from the THP to the left upper first molar is derived.

14. The method of claim 2, wherein the machine learning algorithm detects the nasion in the CBCT image in the coronal plane, and the crown tip of the upper incisor and the root tip of the upper incisor in the incisor image in a cross-sectional view, and wherein the degree of inclination of the upper central incisor is derived through an angle between the THP and a vector connecting the crown tip of the upper incisor and the root tip of the upper incisor.

15. The method of claim 2, wherein the machine learning algorithm detects a menton, which is a lowest point in the mandible, and a gonion, which is a point of maximum curvature in the mandibular angle, in the CBCT image in the sagittal plane, and the crown tip of the lower incisor and the root tip of the lower incisor in the incisor image in a cross-sectional view, and wherein the degree of inclination of the lower central incisor is derived through an angle between a MeGo line connecting the menton and the gonion and a vector connecting the crown tip of the lower incisor and the root tip of the lower incisor.

16. The method of claim 2, wherein the machine learning algorithm detects the nasion, a menton, which is a lowest point in the mandible, and a gonion, which is a point of maximum curvature in the mandibular angle, in the CBCT image in the sagittal plane, and wherein, through an angle between the THP and a MeGo line connecting the menton and the gonion, the degree of inclination of the mandible with respect to the THP is derived.

17. The method of claim 1, further comprising:

diagnosing a facial profile of the patient or an occlusal state in response to the derived 13 parameters.

18. The method of claim 17, wherein when the patient's occlusal state is diagnosed corresponding to the derived 13 parameters, a state in which an antero-posterior occlusal position of the maxilla and mandible is in a relatively normal category, a state in which the maxilla relatively protrudes relative to the mandible, and a state in which the mandible relatively protrudes relative to the maxilla are classified and diagnosed, respectively.

19. The method of claim 17, wherein when a facial profile of the patient is diagnosed corresponding to the derived 13 parameters, a state in which a length of the facial portion is in a normal category, a state in which the length of the facial portion is shorter than the normal category, and a state in which the length of the facial portion is longer than the normal category are classified and diagnosed respectively.

20. A non-transitory computer readable recording medium storing thereon a computer program, which when executed by a computer, performs a method of deriving cephalometric parameters for orthodontic diagnosis based on machine learning, the method comprising:

obtaining 3D cone beam computed tomography (CBCT) images for orthodontic diagnosis including a CBCT image in a sagittal plane, a CBCT image in a coronal plane, a dental panoramic image, and an incisor image in a cross-sectional view, respectively, for a patient from 3D CBCT image data captured of the patient's head at a natural head position;

detecting a plurality of cephalometric landmarks on the 3D CBCT images based on a machine learning algorithm; and deriving 13 parameters corresponding to distances or angles between the detected plurality of cephalometric landmarks, wherein at least one of the 13 parameters is derived using one of a nasion true vertical plane (NTVP) and a true horizontal plane (THP) among the plurality of cephalometric landmarks, wherein the NTVP is a vertical plane passing through a nasion, the THP is a horizontal plane passing through the nasion, and the nasion is a most concave point between a frontal bone and a nasal bone.

* * * * *